(12) United States Patent
Yin

(10) Patent No.: US 11,974,874 B2
(45) Date of Patent: *May 7, 2024

(54) SYSTEM AND METHOD FOR LOCATING A TARGET SUBJECT

(71) Applicant: SHANGHAI UNITED IMAGING HEALTHCARE CO., LTD., Shanghai (CN)

(72) Inventor: Hui Yin, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/171,655

(22) Filed: Feb. 20, 2023

(65) Prior Publication Data

US 2023/0200772 A1 Jun. 29, 2023

Related U.S. Application Data

(60) Continuation of application No. 17/305,667, filed on Jul. 12, 2021, now Pat. No. 11,583,240, which is a
(Continued)

(30) Foreign Application Priority Data

Sep. 25, 2017 (CN) .......................... 201710874065.2
Nov. 30, 2017 (CN) .......................... 201711242643.7
(Continued)

(51) Int. Cl.
*A61B 6/00* (2006.01)
*A61B 6/04* (2006.01)
(Continued)

(52) U.S. Cl.
CPC ............ *A61B 6/547* (2013.01); *A61B 6/0407* (2013.01); *A61B 6/0492* (2013.01); *A61B 6/12* (2013.01);
(Continued)

(58) Field of Classification Search
None
See application file for complete search history.

(56) References Cited

U.S. PATENT DOCUMENTS 3,991,310 A 11/1976 Morrison
4,884,293 A 11/1989 Koyama
(Continued)

FOREIGN PATENT DOCUMENTS

CN 2234758 Y 9/1996
CN 2836728 Y 11/2006
(Continued)

OTHER PUBLICATIONS

International Search Report in PCT/CN2018/107434 dated Jan. 4, 2019, 5 pages.
(Continued)

*Primary Examiner* — Hoon K Song
(74) *Attorney, Agent, or Firm* — METIS IP LLC

(57) ABSTRACT

The present disclosure relates to a system and method for locating a target subject associated with an X-ray system. The X-ray system may include an X-ray source, a detection component, an arm, and a platform. The X-ray system may also include a first positioning component, a second positioning component, or a third positioning component. The first positioning component may be configured to determine a target point where a region of interest (ROI) of the target subject locates. The second positioning component may be configured to locate the target subject. The third positioning component may be configured to obtain location information
(Continued)

of a target device associated with the target subject in real-time.

18 Claims, 24 Drawing Sheets

Related U.S. Application Data division of application No. 16/236,460, filed on Dec. 29, 2018, now Pat. No. 11,058,389, which is a continuation of application No. PCT/CN2018/107434, filed on Sep. 25, 2018.

(30) Foreign Application Priority Data

Dec. 20, 2017  (CN) .................. 201711384644.5
Jun. 26, 2018  (CN) .................. 201810671197.X

(51) Int. Cl.
*A61B 6/12* (2006.01)
*A61B 34/20* (2016.01)
*A61B 6/08* (2006.01)
*A61B 90/00* (2016.01)

(52) U.S. Cl.
CPC ............ *A61B 6/4441* (2013.01); *A61B 34/20* (2016.02); *A61B 6/08* (2013.01); *A61B 2034/2051* (2016.02); *A61B 2034/2055* (2016.02); *A61B 2090/365* (2016.02); *A61B 2090/366* (2016.02); *A61B 2090/372* (2016.02); *A61B 2090/376* (2016.02)

(56) References Cited

U.S. PATENT DOCUMENTS

| | | | |
|---|---|---|---|
| 5,690,107 A | 11/1997 | Hofmann | |
| 6,048,097 A | 4/2000 | Heinze | |
| 6,447,163 B1* | 9/2002 | Bani-Hashemi | G01N 23/046 378/205 |
| 6,527,443 B1 | 3/2003 | Vilsmeier et al. | |
| 6,640,127 B1 | 10/2003 | Kosaka et al. | |
| 7,519,415 B2 | 4/2009 | Mitschke et al. | |
| 7,853,311 B1 | 12/2010 | Webb | |
| 11,058,389 B2* | 7/2021 | Yin | A61B 34/20 |
| 2003/0072416 A1 | 4/2003 | Rasche et al. | |
| 2005/0163279 A1 | 7/2005 | Mitschke et al. | |
| 2005/0195945 A1 | 9/2005 | Gotoh | |
| 2007/0189456 A1 | 8/2007 | Haras | |
| 2008/0181359 A1 | 7/2008 | Stayman et al. | |
| 2009/0086927 A1 | 4/2009 | Wang et al. | |
| 2009/0190722 A1 | 7/2009 | Windt | |
| 2009/0252290 A1 | 10/2009 | Plut et al. | |
| 2009/0278702 A1 | 11/2009 | Graumann et al. | |
| 2010/0054402 A1 | 3/2010 | Fischer et al. | |
| 2010/0246778 A1 | 9/2010 | Heigl et al. | |
| 2011/0087089 A1 | 4/2011 | Meinel et al. | |
| 2011/0096907 A1 | 4/2011 | Mohamed | |
| 2013/0066196 A1 | 3/2013 | Graumann et al. | |
| 2013/0089180 A1* | 4/2013 | Graumann | A61B 6/08 378/62 |
| 2013/0096421 A1* | 4/2013 | Welch | A61B 6/022 600/424 |
| 2014/0188132 A1 | 7/2014 | Kang | |
| 2014/0348296 A1 | 11/2014 | Goossen et al. | |
| 2015/0126796 A1 | 5/2015 | Yan et al. | |
| 2015/0201892 A1 | 7/2015 | Hummel et al. | |
| 2015/0351712 A1 | 12/2015 | Ohishi | |
| 2016/0158082 A1 | 6/2016 | Gainor et al. | |
| 2016/0166333 A1 | 6/2016 | Wang et al. | |
| 2016/0278731 A1 | 9/2016 | Babic et al. | |
| 2016/0302871 A1 | 10/2016 | Gregerson et al. | |
| 2017/0156800 A1 | 6/2017 | Brown | |
| 2017/0215985 A1 | 8/2017 | Kubiak et al. | |
| 2017/0325897 A1 | 11/2017 | Isaacs et al. | |
| 2018/0333208 A1 | 11/2018 | Kotian et al. | |
| 2020/0085521 A1 | 3/2020 | Nikou et al. | |

FOREIGN PATENT DOCUMENTS

| | | |
|---|---|---|
| CN | 201324245 Y | 10/2009 |
| CN | 101637393 A | 2/2010 |
| CN | 101647710 A | 2/2010 |
| CN | 101791246 A | 8/2010 |
| CN | 201847692 U | 6/2011 |
| CN | 102961189 A | 3/2013 |
| CN | 202859934 U | 4/2013 |
| CN | 103126703 A | 6/2013 |
| CN | 203458398 U | 3/2014 |
| CN | 203736217 U | 7/2014 |
| CN | 104161539 A | 11/2014 |
| CN | 203988389 U | 12/2014 |
| CN | 204207844 U | 3/2015 |
| CN | 104739434 A | 7/2015 |
| CN | 106073895 A | 11/2016 |
| CN | 106344053 A | 1/2017 |
| CN | 106562795 A | 4/2017 |
| CN | 206183369 U | 5/2017 |
| CN | 206275695 U | 6/2017 |
| CN | 106974673 A | 7/2017 |
| CN | 107582147 A | 1/2018 |
| CN | 107773262 A | 3/2018 |
| CN | 107898500 A | 4/2018 |
| DE | 19717109 A1 | 4/1998 |
| DE | 29918903 U1 | 1/2000 |
| DE | 202004009139 U1 | 9/2004 |
| DE | 10335656 A1 | 3/2005 |
| DE | 102004028366 A1 | 1/2006 |
| DE | 102006026945 A1 | 12/2007 |
| EP | 0913169 B1 | 7/2004 |
| JP | 2006280844 A | 10/2006 |
| RU | 2553505 C1 | 6/2015 |
| WO | 0180738 A1 | 11/2001 |
| WO | 2009077480 A1 | 6/2009 |
| WO | 2012149548 A2 | 11/2012 |
| WO | 2014106262 A1 | 7/2014 |
| WO | 2015132069 A1 | 9/2015 |
| WO | 2016023599 A1 | 2/2016 |
| WO | 2016122957 A1 | 8/2016 |
| WO | 2017134546 A2 | 8/2017 |

OTHER PUBLICATIONS

Written Opinion in PCT/CN2018/107434 dated Jan. 4, 2019, 5 pages.
First Office Action in Chinese Application No. 201710874065.2 dated Aug. 28, 2019, 16 pages.
First Office Action in Chinese Application No. 201711384644.5 dated May 27, 2019, 15 pages.
The Second Office Action in Chinese Application No. 201711384644.5 dated Mar. 10, 2020, 14 pages.
The Third Office Action in Chinese Application No. 201711384644.5 dated Aug. 12, 2020, 16 pages.
First Office Action in Chinese Application No. 201810671197.X dated Jun. 16, 2020, 23 pages.
The Extended European Search Report in European Application No. 18858220.9 dated Oct. 5, 2020, 10 pages.
The Extended European Search Report in European Application No. 20189492.0 dated Dec. 8, 2020, 11 pages.
The Extended European Search Report in European Application No. 20189493.8 dated Nov. 27, 2020, 8 pages.
Notification to Grant Patent Right for Invention in Chinese Application No. 201711384644.5 dated Mar. 2, 2021, 5 pages.
Office Action in Russian Application No. 2020114681 dated Dec. 27, 2021, 16 pages.

* cited by examiner

700

```
┌─────────────────────────────────────────────────────────┐
│     Rotating a C-shaped arm to a front position         │─710
└─────────────────────────────────────────────────────────┘
                            │
                            ▼
┌─────────────────────────────────────────────────────────┐
│   Initiating a first laser component and a second laser │─720
│                      component                          │
└─────────────────────────────────────────────────────────┘
                            │
                            ▼
┌─────────────────────────────────────────────────────────┐
│ Determining a target point based on an intersection between│
│ a first laser beam emitted by the first laser component and a│─730
│  second laser component emitted by the second laser     │
│                      component                          │
└─────────────────────────────────────────────────────────┘
```

FIG. 7

SYSTEM AND METHOD FOR LOCATING A TARGET SUBJECT

CROSS-REFERENCE TO RELATED APPLICATIONS

This application is a continuation of U.S. application Ser. No. 17/305,667, filed on Jul. 12, 2021, which is a division of U.S. application Ser. No. 16/236,460 (now U.S. Pat. No. 11,058,389), filed on Dec. 29, 2018, which is a Continuation of International Application No. PCT/CN2018/107434, filed on Sep. 25, 2018, which claims priority to Chinese Patent Application No. 201710874065.2 filed on Sep. 25, 2017, Chinese Patent Application No. 201711242643.7 filed on Nov. 30, 2017, Chinese Patent Application No. 201711384644.5 filed on Dec. 20, 2017, and Chinese Patent Application No. 201810671197.X filed on Jun. 26, 2018. Each of the above-referenced applications is incorporated herein by reference in its entirety.

TECHNICAL FIELD

The present disclosure generally relates to a medical system, and more particularly, to a system and method for locating a target subject in a medical or imaging procedure.

BACKGROUND

In a surgical operation (e.g., a puncturing surgery), an operator may perform the surgical operation at a lesion point (e.g., a puncturing point) associated with a target subject (e.g., a patient). An anatomical image may be determined by emitting X-rays towards the target subject by a medical imaging system, which may assist the operator to determine the lesion point. In some cases, the lesion point may be determined based on the anatomical image and clinical experience of the operator, which may be relatively inefficient or inaccurate. In some cases, in the surgical operation, anatomical images from different perspectives may be needed, and the operator may need to adjust the radiation of the X-rays (e.g., a direction of the X-rays) to ensure the lesion point at or near to the center of the anatomical image from the different perspectives. In some cases, in order to navigate the surgical operation in real-time (e.g., navigate an operation equipment), at least one additional device (e.g., a trolley) used for placing the navigation device in an operation room. In one hand, the additional device may occupy the space of the operation room. In the other hand, the additional device may have to register with the medical imaging system before navigation, which may be inefficient. Thus, it may be desirable to develop a method or a system to locate the target subject or the target device in a medical imaging procedure.

SUMMARY

In one aspect of the present disclosure, an X-ray system may be provided. The X-ray system may include an X-ray source configured to emit an X-ray beam towards a target subject; a detection component configured to receive at least a portion of the X-ray beam that transmits through the target subject; an arm configured to support the detection component and the X-ray source; a platform configured to place the target subject, the platform being situated between the X-ray source and the detection component; and a first positioning component configured to determine a target point where a region of interest (ROI) of the target subject locates, wherein: the first positioning component includes a first laser component configured to emit a first laser beam, and a second laser component configured to emit a second laser beam, wherein said first and second laser beam intersect at the target point.

In some embodiments, the arm may comprise a group selected from a C-arm and a G-arm.

In some embodiments, the target point may locate at an intersection of a first X-ray beam emitted by the X-ray source when the arm is at a front position and a second X-ray beam emitted by the X-ray source when the arm is at a lateral position.

In some embodiments, the target point may locate at an intersection between a central axis of said first X-ray beam and a central axis of said second X-ray beam.

In some embodiments, the first laser component may be mounted on an area selected from the X-ray source and the detection component.

In some embodiments, the first laser component may be mounted on an outer side of the detection component.

In some embodiments, the second laser component may be mounted on an inner side of the arm.

In some embodiments, one of the first laser beam and the second laser beam may have a shape of crisscross, and the other one has a shape of slot.

In some embodiments, the first laser beam or the second laser beam with the shape of crisscross may be emitted by a crisscross laser generator or by two perpendicular slotted laser generators.

In some embodiments, the system may also include: a position detecting device configured to detect a rotation angle of the arm, wherein the positioning detecting device is mounted on the arm; and a prompting device configured to prompt the rotation angle, wherein the prompting device is connected to the position detecting device.

In some embodiments, the system may also include: a third laser emitting component configured to emit a third laser beam with a first predetermined pattern on the target subject; and a second positioning component being situated between the detection component and the platform, wherein the first predetermined pattern being projected on the second positioning component coincides with a pattern of the second positioning component, and the second positioning component is configured to locate the target subject based on the first predetermined pattern and an anatomical image associated with the target subject determined by projecting the X-ray beam towards the target subject.

In some embodiments, a first travel path of the third laser beam emitted by the third laser emitting component may coincide with a second travel path of the X-ray beam emitted by the X-ray source.

In some embodiments, the system may also include a third positioning component configured to: obtain location information of a target device associated with the target subject in real-time.

In some embodiments, the third positioning component may include at least two positioning detectors.

In a second aspect of the present disclosure, an X-ray system is provided. The X-ray system may include: an X-ray source configured to emit an X-ray beam towards a target subject; a detection component configured to receive at least a portion of the X-ray beam that transmits through the target subject; an arm configured to support the detection component and the X-ray source; a platform configured to place the target subject, the platform being situated between the X-ray source and the detection component; a laser emitting component configured to emit a laser beam with a first predetermined pattern on the target subject; and a positioning component being situated between the detection component and the platform, wherein the first predetermined pattern being projected on the positioning component coincides with a pattern of the positioning component, and the positioning component is configured to locate the target subject based on the first predetermined pattern and an anatomical image associated with the target subject determined by projecting the X-ray beam towards the target subject.

In some embodiments, the arm may comprise a group selected from C-arm and a G-arm.

In some embodiments, the first predetermined pattern may comprise girds selected from a group selected from regular lines, grids including regular polygons, grids including irregular polygons, grids including regular curves, and grids including circles.

In some embodiments, a first travel path of said laser beam may coincide with a second travel path of said X-ray beam.

In some embodiments, the laser emitting component may be mounted on the X-ray source.

In some embodiments, the X-ray source may include: an X-ray component configured to emit the X-ray beam towards the target subject; and a laser controlling component underneath of the X-ray component, comprising: a reflector and the laser emitting component, the first travel path of the laser beam emitted by the laser emitting component after reflected by the reflector coinciding with the second travel path of the X-ray beam.

In some embodiments, the positioning component may include at least one positioning marker, and the at least one positioning marker is configured to locate the target subject.

In some embodiments, the at least one positioning marker may include at least one laser marker.

In some embodiments, the at least one positioning marker may locate on at least one intersection of the grids of the first predetermined pattern.

In some embodiments, the positioning component may be situated on a surface of the detection component facing the platform.

In some embodiments, the system may also include: a movement device configured to move the positioning component away from the surface of the detection component facing the platform.

In some embodiments, the movement device includes: a transmission mechanism configured to move the positioning component, the transmission mechanism being connected to the positioning component.

In some embodiments, the positioning component may be placed on the detection component or wounded by the transmission mechanism.

In some embodiments, the transmission mechanism may comprise at least one transmission wheel, and wherein the transmission mechanism is connected to the positioning component through the at least one transmission wheel.

In some embodiments, the system may also include: a second positioning component configured to: obtain location information of a target device associated with the target subject in real-time.

In some embodiments, the second positioning component may include at least one positioning detector.

In a third aspect of the present disclosure, an X-ray system is provided. The X-ray system may include: an X-ray source configured to emit an X-ray beam towards a target subject; a detection component configured to receive at least a portion of the X-ray beam that transmits through the target subject; an arm configured to support the detection component and the X-ray source; a platform configured to place the target subject, the platform being situated between the X-ray source and the detection component; and a positioning component configured to: obtain location information of a target device associated with the target subject in real-time.

In some embodiments, the arm may comprise a group selected from a C-arm and a G-arm.

In some embodiments, the target device associated with the target subject may comprise an operation equipment.

In some embodiments, the positioning component may comprise at least two positioning detectors.

In some embodiments, the at least two positioning detectors may be able to move to adjust at least two distances between the at least two positioning detectors.

In some embodiments, the positioning component may include at least one reciprocating rod, wherein an end of each of the at least one reciprocating rod is mounted on the arm.

In some embodiments, the each of the at least one reciprocating rod may correspond to each of the positioning detector.

In some embodiments, the third positioning component may include at least one slide rail, wherein the at least one slide rail is mounted on the arm.

In some embodiments, the positioning detector may slide through the at least one slide rail.

In some embodiments, the slide rail may include a reciprocating slide rail.

In some embodiments, the positioning component may be mounted on the detection component or the X-ray source.

In some embodiments, the positioning component may be slidably mounted on the arm.

In some embodiments, the arm may accommodate the at least one slide rail.

In some embodiments, the positioning detector may include at least one slide block matched with the at least one slide rail.

In some embodiments, the positioning detector may include an optic positioning detector.

In a fourth aspect of the present disclosure, a positioning method of an X-ray system may be provided. The X-ray system may include an X-ray source, a detection component, an arm, a platform, a first positioning component including a first laser component, and a second laser component, and the positioning method comprising: rotating the arm to a front position; initiating the first laser component and the second laser component; and determining a target point based on an intersection between a first laser beam emitted by the first laser component and a second laser component emitted by the second laser component.

In a fifth aspect of the present disclosure, a positioning method of an X-ray system may be provided. The X-ray system may include an X-ray source, a detection component, an arm, a platform, a positioning component, and a laser emitting component, and the positioning method comprising: mounting the positioning component between the detection component and a target subject; obtaining an overlaid image including an anatomical image associated with the target subject determined by projecting a detection beam towards the target subject and a pattern of the positioning component formed on a surface of the target subject; determining a lesion point associated with the target subject based on the overlaid image and a first predetermined pattern determined by projecting a positioning beam to the target subject by the laser emitting component; and determining a target point corresponding to the lesion point based on the overlaid image and the first predetermined pattern.

In a sixth aspect of the present disclosure, a positioning method of an X-ray system is provided. The X-ray system may include an X-ray source, a detection component, an arm, and a platform, and the positioning method comprising: determining an anatomical image associated with a target subject by projecting a detection beam towards the target subject; overlapping a first pattern on the anatomical image; forming a second pattern on a surface of the target subject by projecting a positioning beam to the target subject, wherein the first pattern coincides with the second pattern; and determining a target point based on the anatomical image and the second pattern.

In some embodiments, the first pattern or the second pattern may include grids.

In some embodiments, wherein determining said target point based on the anatomical image and the second pattern includes: determining a lesion point associated with the target subject based on the anatomical image; and determining the target point on the grids of the second pattern based on the lesion point.

In some embodiments, wherein determining said lesion point associated with the target subject based on the anatomical image includes: obtaining diagnostic information associated with the target subject; and determining the lesion point associated with the target subject based on the diagnostic information.

In some embodiments, the method may also include showing the diagnostic information associated with the target subject on the anatomical image.

In some embodiments, wherein determining the target point on the grids of the second pattern based on the lesion point includes: determining a relationship between a plurality of first points on the grids of the first pattern and a plurality of second points corresponding to the plurality of first points on the grids of the second pattern.

In some embodiments, the method may also include marking the target point by projecting a marking beam or the positioning beam to the target point.

In some embodiments, the marking beam is emitted by a laser device mounted on the arm.

In some embodiments, the target point may be a point where a surgical operation is performed.

In some embodiments, the method may also include adjusting the positioning beam based on the first pattern and the second pattern projected by the positioning beam.

In some embodiments, wherein adjusting the positioning beam based on the first pattern and the second pattern projected by the positioning beam includes: adjusting the positioning beam if the second pattern projected by the positioning beam does not coincide with the first pattern.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 7 is a flowchart illustrating an exemplary process for determining a target point where a region of interest (ROI) of the target subject locates according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
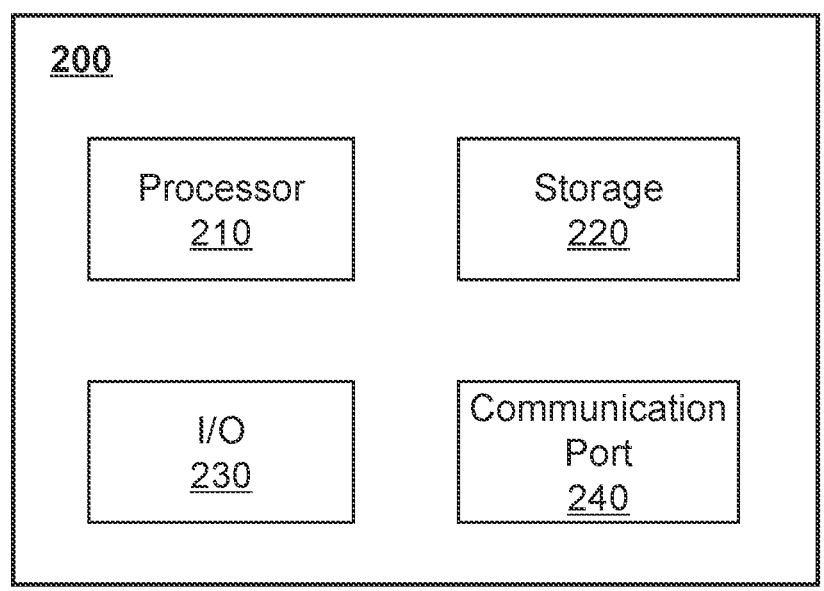
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

The present disclosure relates to a system and method for locating a target subject associated with an X-ray system. The X-ray system may include an X-ray source, a detection component, an arm, and a platform. The X-ray system may also include at least one positioning component (e.g., a first positioning component, a second positioning component, a third positioning component). The first positioning component may be configured to determine a target point where a region of interest (ROI) of the target subject locates. The first positioning component may include a first laser component configured to emit a first laser beam, and a second laser component configured to emit a second laser beam. The first laser beam and the second laser beam may intersect at the target point. The second positioning component may be configured to locate the target subject. The second positioning component may be situated between the detection component and the platform. The third positioning component may be configured to obtain location information of a target device (e.g., an operation equipment) associated with the target subject in real-time.

Figure 1:
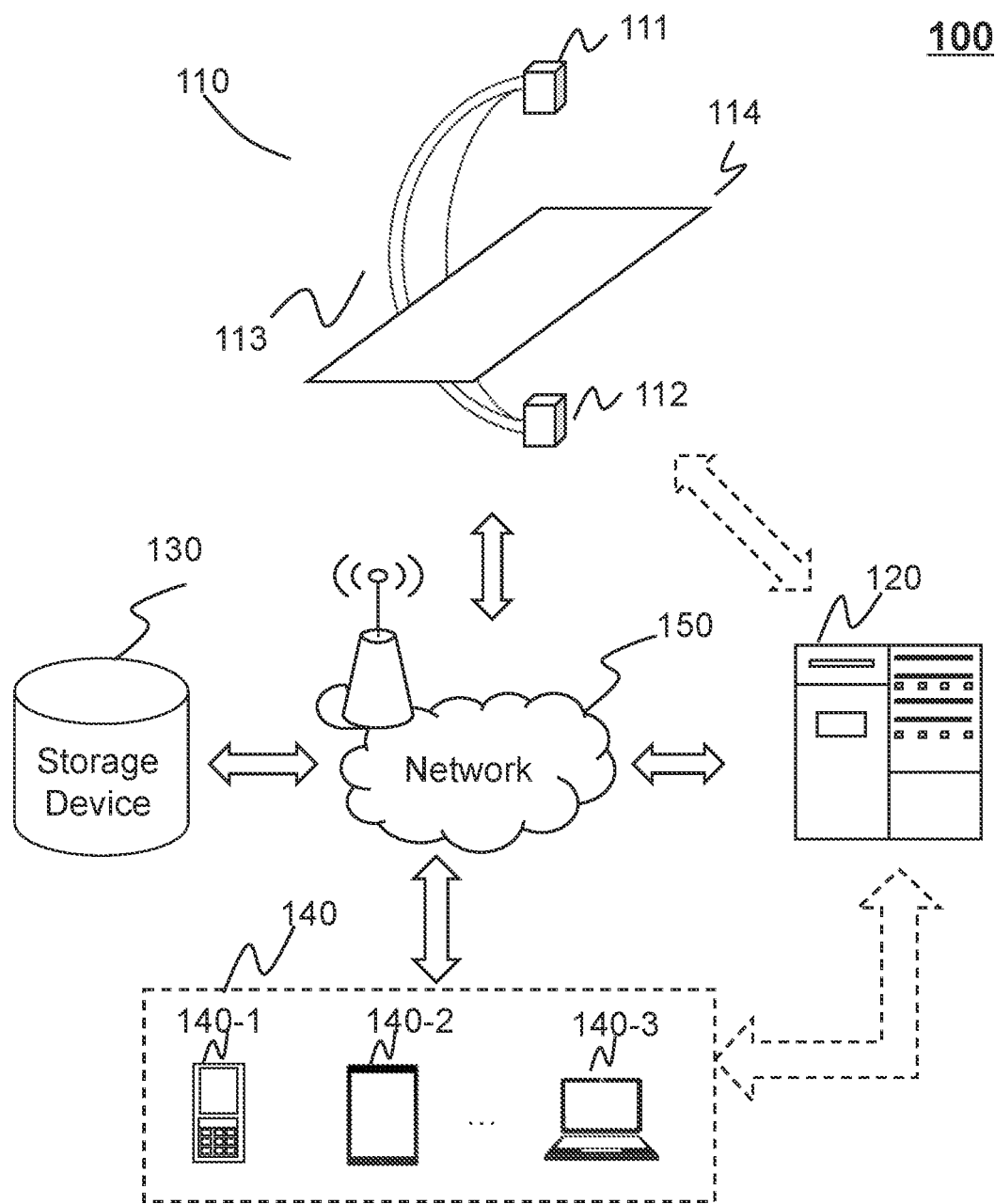
FIG. 1 is a schematic diagram illustrating an exemplary X-ray system according to some embodiments of the present disclosure.

FIG. 1 is a schematic diagram illustrating an exemplary X-ray system according to some embodiments of the present disclosure. The X-ray system 100 may include an X-ray imaging apparatus 110, a processing device 120, a storage device 130, a terminal 140, and a network 150. The components of the X-ray system 100 may be connected to each other in various ways. Merely by way of example, the X-ray imaging apparatus 110 may be connected to the processing device 120 via the network 150. As another example, the X-ray imaging apparatus 110 may be connected to the processing device 120 directly. As a further example, the storage device 130 may be connected to the processing device 120 directly or via the network 150. As still a further example, the terminal 140 may be connected to the processing device 120 directly or via the network 150.

The X-ray imaging apparatus 110 may include an X-ray source 111 (also referred to as an X-ray tube), a detection component 112, a C-arm 113, and a platform 114. The X-ray source 111 and the detection component 112 may be mounted on the C-arm 113. The C-arm 113 may include a first end and a second end arranged opposite to each other. For example, the X-ray source 111 may be mounted on the first end of the C-arm 113 and the detection component 112 may be mounted on the second end of the C-arm 113. Alternatively, the X-ray source 111 may be mounted on the second end of the C-arm 113 and the detection component 112 may be mounted on the first end of the C-arm 113.

The platform 114 may hold or support a subject. The subject may be a biological subject (e.g., a patient, an animal) or a non-biological subject (e.g., a man-made subject). The X-ray source 111 may emit X-rays (also referred to as "X-ray beam") towards the subject, and the X-rays may attenuate when passing through the subject. The detection component 112 may receive the attenuated X-rays that pass through the subject and generate readings (also referred to as scanning data) corresponding to the received X-rays. In some embodiments, the detection component 112 may include a scintillation detector (e.g., a cesium iodide detector), a gas detector, a circular detector, a square detector, an arcuate detector, or the like, or any combination thereof. The detection component 112 may be a single-row detector or a multiple-row detector.

In some embodiments, the processing device 120 may process data obtained from the X-ray imaging apparatus 110, the storage device 130, or the terminal 140. For example, the processing device 120 may obtain scanning data related to a subject. The processing device 120 may further process the scanning data to generate an anatomical image of the subject. As another example, the processing device 120 may determine a target point where a region of interest (ROI) of the subject locates. As a further example, the processing device 120 may determine location information of a target device (e.g., an operation equipment) associated with the subject in real-time.

The processing device 120 may include a central processing unit (CPU), a digital signal processor (DSP), a system on a chip (SoC), a microcontroller unit (MCU), or the like, or any combination thereof. In some embodiments, the processing device 120 may be a single server or a server group. The server group may be centralized or distributed. In some embodiments, the processing device 120 may be local or remote. For example, the processing device 120 may access information and/or data stored in the X-ray imaging apparatus 110, the storage device 130, and/or the terminal 140 via the network 150. As another example, the processing device 120 may be directly connected to the X-ray imaging apparatus 110, the storage device 130, and/or the terminal 140, to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data and/or instructions. In some embodiments, the storage device 130 may store data obtained from the processing device 120 and/or the terminal 140. In some embodiments, the storage device 130 may store data and/or instructions that the processing device 120 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more components of the X-ray system 100 (e.g., the terminal 140, the processing device 120). One or more components of the X-ray system 100 may access the data or instructions stored in the storage device 130 via the network 150. In some embodiments, the storage device 130 may be directly connected to or communicate with one or more components of the X-ray system 100 (e.g., the terminal 140, the processing device 120). In some embodiments, the storage device 130 may be part of the processing device 120.

The terminal 140 include a mobile device 140-1, a tablet computer 140-2, a laptop computer 140-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 140 may remotely operate the X-ray imaging apparatus 110. In some embodiments, the terminal 140 may operate the X-ray imaging apparatus 110 via a wireless connection. In some embodiments, the terminal 140 may receive information and/or instructions inputted by a user, and send the received information and/or instructions to the X-ray imaging apparatus 110 or to the processing device 120 via the network 150. In some embodiments, the terminal 140 may receive data and/or information from the processing device 120. In some embodiments, the terminal 140 may be part of the processing device 120. In some embodiments, the terminal 140 may be omitted.

The network 150 may facilitate exchange of information and/or data. In some embodiments, one or more components of the X-ray system 100 (e.g., the X-ray imaging apparatus 110, the terminal 140, the processing device 120, or the storage device 130) may send information and/or data to another component(s) in the X-ray system 100 via the network 150. In some embodiments, the network 150 may be any type of wired or wireless network, or combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired or wireless network access points such as base stations and/or internet exchange points through which one or more components of the X-ray system 100 may be connected to the network 150 to exchange data and/or information.

It should be noted that the above description of the X-ray system 100 is provided for the purposes of illustration, and is not intended to limit the scope of the present disclosure. For persons having ordinary skills in the art, multiple variations and modifications may be made under the teachings of the present disclosure. However, those variations and modifications shall not depart from the scope of the present disclosure. For example, the X-ray system 100 may include any other shape of arm, e.g., a G-arm, etc.

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the X-ray imaging apparatus 110, the terminal 140, the storage device 130, and/or any other component of the MRI system 100. Specifically, the processor 210 may process one or more measured data sets obtained from the X-ray imaging apparatus 110. For example, the processor 210 may perform one-dimensional (1D) correction or two-dimensional (2D) correction for the measured data set(s). The processor 210 may reconstruct an image based on the corrected data set(s). In some embodiments, the reconstructed image may be stored in the storage device 130, the storage 220, etc. In some embodiments, the reconstructed image may be displayed on a display device by the I/O 230. In some embodiments, the processor 210 may perform instructions obtained from the terminal 140. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the X-ray imaging apparatus 110, the terminal 140, the storage device 130, or any other component of the MRI system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for reducing or removing one or more artifacts in an image.

The I/O 230 may input or output signals, data, and/or information. In some embodiments, the I/O 230 may enable a user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the X-ray imaging apparatus 110, the terminal 140, or the storage device 130. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
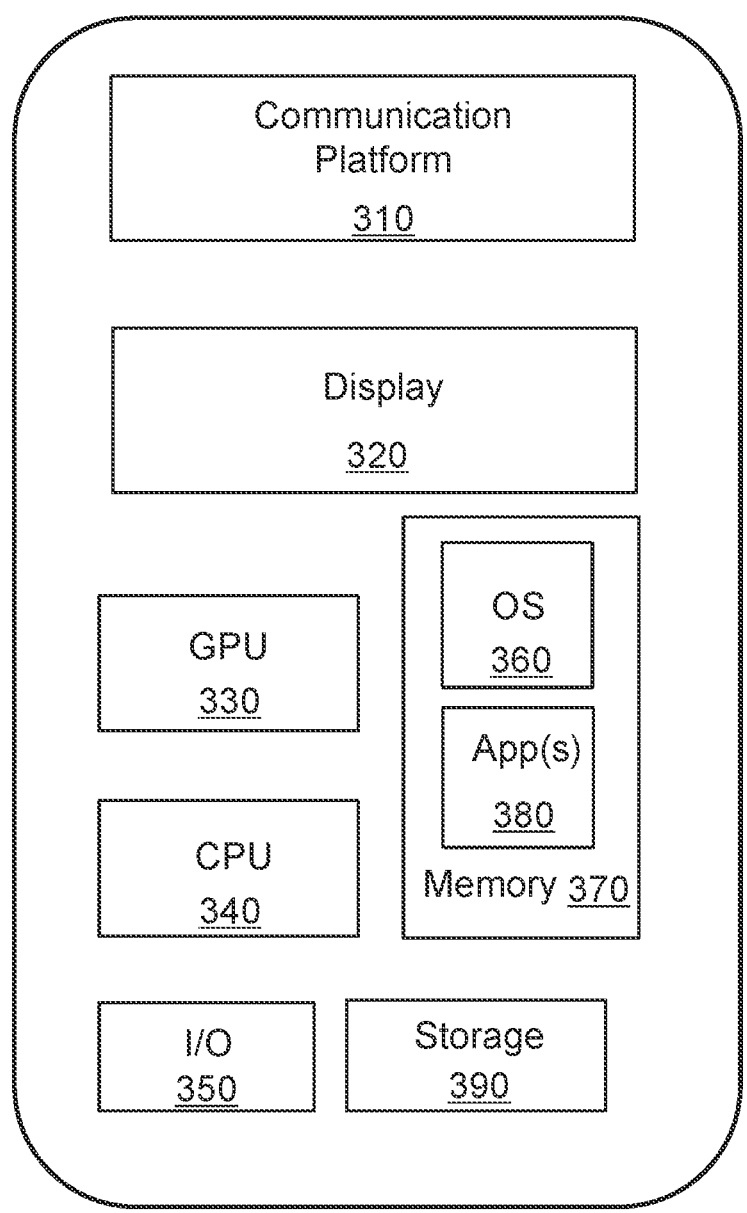
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image with reduced Nyquist ghost artifact as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 4:
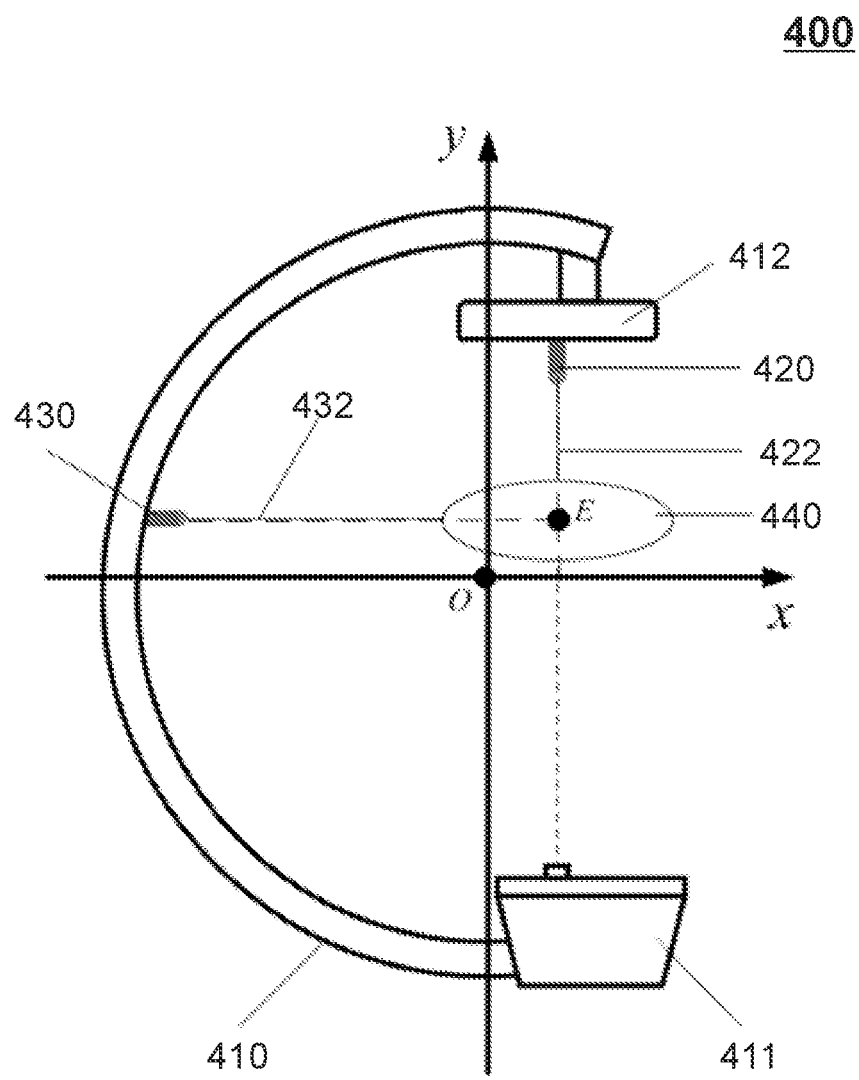
FIG. 4 is a schematic diagram illustrating an exemplary X-ray system at a front position according to some embodiments of the present disclosure.
Figure 5:
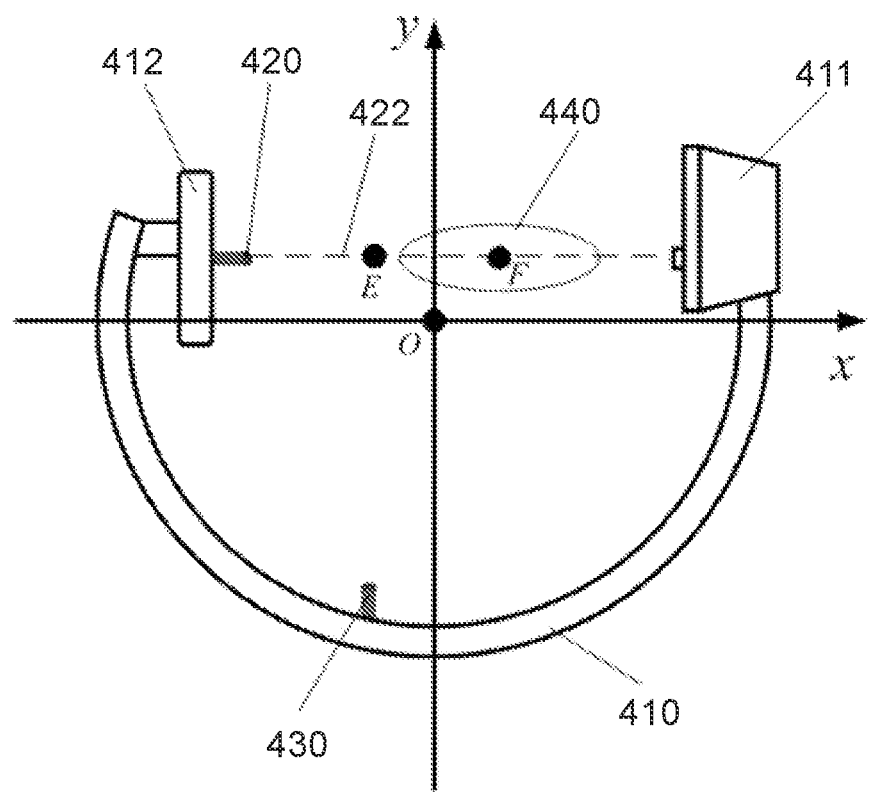
FIG. 5 is a schematic diagram illustrating the exemplary X-ray system at a lateral position according to some embodiments of the present disclosure.

FIG. 4 is a schematic diagram illustrating an exemplary X-ray system at a front position, and FIG. 5 is a schematic diagram illustrating the exemplary X-ray system at a lateral position according to some embodiments of the present disclosure. The X-ray system 400 may include an C-arm 410, an X-ray source 411, a detection component 412, and a platform (not shown). The X-ray source 411 may be configured to emit X-rays toward a target subject. The detection component 412 may be configured to receive at least a portion of the X-rays that transmit through the target subject. The platform may be configured to place the target subject, and the platform may be situated between the X-ray source 411 and the detection component 412. The C-arm 410 may be configured to support the detection component 412 and the X-ray source 411.

The C-arm 410 may be non-isocentric. The C-arm 410 may be configured with at least two perspectives (e.g., a first perspective, a second perspective). The C-arm 410 may be rotated from one perspective to another perspective around the center of the C-arm 410. The X-ray system 400 may be configured to determine an anatomical image from each perspective by scanning at least a portion of the target subject. The anatomical image may show a health condition of a region of interest (ROI) 440 of a target subject. The X-ray system 400 may also include a first positioning component. The first positioning component may be configured to determine a target point where the ROI 440 of the target subject locates, thereby placing the center of the ROI 440 at or near to the target point before the scanning and then obtaining an anatomical image of which the ROI 440 is near to or at the center. Specifically, the first positioning component may be configured to simplify the process for locating the ROI 440 in the at least two perspectives.

The first positioning component may include a first laser component 420 and a second laser component 430. The first laser component 420 may be mounted on the X-ray source 411 or the detection component 412. The first laser component 420 may be configured to emit a first laser beam 422. A travel path of the first laser beam 422 may coincide with the X-rays emitted by the X-ray source 411 by adjusting a mounting location and/or an emitting angle of the first laser component 420. Therefore, the first laser beam 422 may be configured to identify a travel path of the X-rays emitted by the X-ray source 411. The second laser component 430 may be mounted on an inner position of the C-arm 410. The second laser component 430 may be configured to emit a second laser beam 432. The second laser beam 432 and the first laser beam 422 may intersect at a point, and the point may be the target point where the ROI 440 of the target subject locates before scanning. Therefore, the ROI 440 may be near to or at the centers of the anatomical images determined at the first perspective and the second perspective.

The configuration of the first positioning component (e.g., the first laser component 420 and the second laser component 430) may facilitate to determine the target point where the ROI 440 of the target subject locates at based on the first laser beam 422 and the second laser beam 432 instead of emitting the X-rays repeatedly to determine anatomical images of the target subjects and adjusting the positions of the C-arm 410 based on the determined anatomical images. When the ROI 440 of the target subject locates at the target point, the ROI 440 may be near to or at the centers of anatomical images determined at the first perspective and the second perspective, and thus, the ROI 440 being outside of the anatomical image or the ROI 440 being a position that is not near to the center of the anatomical image may be avoided.

In some embodiments, an angel between the first laser beam 422 and the second laser beam 432 may be equal to an angle between the first perspective and the second perspective such that the X-rays may pass through the center (e.g., point F shown in FIGS. 4-5) of the ROI 440. For example, the angle may be 90°. Since a travel path of the second laser beam 432 at the first perspective may coincide with a travel path of the X-rays (or the first laser beam 422) at the second perspective, and a distance from an end of the C-arm 410 to the rotation center (e.g., point 0) may remain the same, a distance from the rotation center to the first laser beam 422 may be equal to a distance from the rotation center to the second laser beam 432, which may improve the accuracy to determine the target point where the ROI 440 of the target subject locates.

In some embodiments, the C-arm 410 may be rotated to a plurality of perspectives. A plurality of second laser components 430 may be mounted along the inner side of the C-arm 410. Each second laser component 430 may correspond to two perspectives. Before scanning, an operator (e.g., a doctor) may select two perspectives from the plurality of perspectives based on practical demands. The operator may select a second laser component 430 corresponding to the first laser component 420 from the plurality of second laser components 430 based on the two perspectives. The target point where the ROI 440 of the target subject locates may be determined based on the first laser component 420 and the selected second laser component 430. Therefore, after determining an anatomical image at the first perspective, the C-arm 410 may be directly rotated to the second perspective to determine an anatomical image at the second perspective without any other adjustment of locations, thereby facilitating the process for determining the target point for at least two perspectives.

As shown in FIG. 4. the X-ray system 400 may be at a front position, the C-arm 410 may be in a vertical status, and the detection component 412 may be at an upper end of the C-arm 410. The X-ray source 411 may be at a lower end of the C-arm 410. As shown in FIG. 5, the X-ray system 400 may be at a lateral position, and the C-arm 410 may be in a horizontal status. The detection component 412 may be at a left end of the C-arm 410, and the X-ray source 411 may be at a right end of the C-arm 410. In some embodiments, the X-rays emitted by the X-ray system 400 may be a cone beam. A first X-ray beam emitted by the X-ray source 411 when the C-arm 410 is at the front position and a second X-ray beam emitted by the X-ray source 411 when the C-arm 410 is at the lateral position may have an intersecting area. Therefore, when an intersecting point of the first laser beam 422 emitted by the first laser component 420 and the second laser beam 432 emitted by the second laser component 430 is within the intersecting area, the intersection may be designated as the target point where the ROI 440 of the target subject locates.

In some embodiments, a first center axis of the first X-ray beam and a second center axis of the second X-ray beam may intersect at a point (e.g., point E as illustrated in FIGS. 4-5). The point may be designated as the target point. If the ROI 440 of the target subject is at the target point, the ROI 440 may be at a center of a front image or a lateral image. In some embodiments, one of the first laser beam 422 and the second laser beam 432 may have a shape of crisscross, and the other one may have a shape of slot. Therefore, two planes determined by the laser beam with the shape of crisscross and a plane determined by the laser beam with the shape of slot may intersect at the target point. The X-ray system 400 described above may make locating the target point more accurate and make observation more convenient, thereby avoiding unnecessary radiation towards the target subject and improving working efficiency of an operator (e.g., a doctor).

In some embodiments, the laser beam (e.g., the first laser beam 422, the second laser beam 432) with the shape of crisscross may be emitted by a crisscross laser generator or by two perpendicular slotted laser generators. In some embodiments, the first laser component 420 may include two slotted laser generators configured to emit the laser beam with the shape of crisscross, and the two slotted laser generators may be mounted on the outer side of the detection component 412 respectively. The second laser component 430 may include a slotted laser generator configured to emit the laser beam with the shape of slot. In some embodiments, the first laser component 420 and the second laser component 430 may be point source laser generators, each laser beam generated from which is a straight line. The target point may be determined based on intersection of the two straight lines. The structure of the X-ray system described above may be easier, however, the accuracy of the location of the target point determined by the X-ray system may be lower with respect to the X-ray system including the crisscross laser generator or by two perpendicular slotted laser generators. In some embodiments, the configuration of the first laser component 420 and the second laser component 430 may make a first intersecting line associated with the first laser component 420 near to or coincide with the center of the X-ray beam when the C-arm 410 is at the front position. A sector emitted by the laser generator in the XOY plane and a sector emitted by the laser generator in the ZOY plane may intersect at the first intersecting line. Besides, a sector emitted by the laser generator of the second laser component 430 in the XOY plane may include the point E and a second intersecting line between the point E and an intersecting point of the C-arm 410 along the X-axis.

In some embodiments, the X-ray system 400 may include the first positioning component described above, a position detecting device, and a prompting device (not shown in FIGS. 4-5). The position detecting device may be mounted on the C-arm 410 and configured to detect a rotation angle of the C-arm 410. The prompting device may be mounted on the positioning detecting device and configured to prompt the rotation angle. For example, upon detecting that the C-arm 410 is rotated to the front position or the lateral position, the position detecting device may detect a position of the C-arm 410, and transmit the position to a controller. The controller may control the prompting device to generate a signal to prompt that the C-arm 410 is at the corresponding positions, thereby avoiding the C-arm 410 over-rotating. Moreover, the first laser component 420 and the second laser component 430 may be laser generators, e.g., laser lights, thereby simplifying the X-ray system 400 and the operations and reduce the cost.

Figure 6:
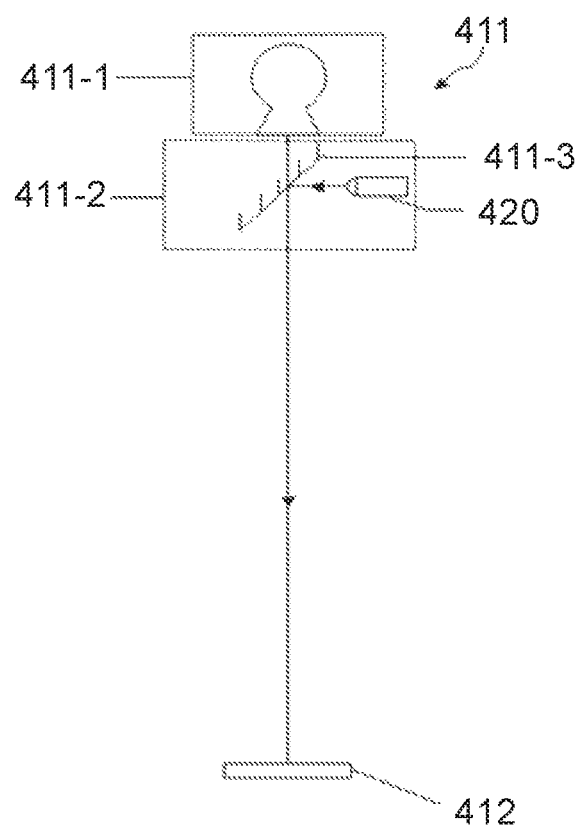
FIG. 6 is a schematic diagram illustrating an exemplary travel path of an X-ray beam emitted by an X-ray source and an exemplary travel path of a first laser beam emitted by a first laser component according to some embodiments.

FIG. 6 is a schematic diagram illustrating an exemplary travel path of an X-ray beam emitted by an X-ray source and an exemplary travel path of a first laser beam emitted by a first laser component according to some embodiments.

As shown in FIG. 6, the X-ray source 411 may include an X-ray component 411-1 and a laser controlling component 411-2. The X-ray component 411-1 may be configured to emit the X-rays towards the target subject. The laser controlling component 411-2 may be underneath of the X-ray component 411-1. The laser controlling component 411-2 may include a reflector 411-3 and the first laser component 420. The reflector 411-3 may be tilted, and the first laser component 420 may be situated on one side of the reflector 411-3. The X-rays emitted by the X-ray component 411-1 may pass through the back surface of the reflector 411-3, thus a travel path of the X-rays emitted by the X-ray component 411-1 may be the same as a travel path of the X-rays after reflected by the reflector 411-3. The first laser beam 422 emitted by the first laser component 420 may pass through the front surface of the reflector 411-3, thus, a travel path of the first laser beam 422 emitted by the first laser component 420 may be different from a travel path of the laser beam 422 after reflected by the reflector 411-3, and the travel path of the laser beam 422 after reflected by the reflector 411-3 may coincide with the travel path of the X-rays emitted by the X-ray component 411-1. The structure of the X-ray source 411 described above may ensure that the travel path of the laser after reflected by the reflector 411-3 may coincide with the travel path of the X-rays emitted by the X-ray component 411-1 and avoid the first laser component 420 being situated underneath the X-ray component 411-1, which may cause to shelter a portion of the X-rays.

In some embodiments, the first laser component 420 may be mounted on the detection component 412, e.g., an outer side of the detection component 412, thereby avoiding to affect the imaging of the detection component 412 and simplifying the structure and mounting of the first laser component 420.

FIG. 7 is a flowchart illustrating an exemplary process for determining a target point where a region of interest (ROI) of the target subject locates according to some embodiments of the present disclosure.

In 710, a C-arm (e.g., the C-arm 410) may be rotated to a front position. The front position may correspond to a first perspective. The first perspective may be selected according to practical demand associated with the ROI (e.g., the ROI 440 described above) of the target subject.

In 720, a first laser component (e.g., the first laser component 420 described above) and a second laser component (e.g., the second laser component 430 described above) may be initiated. The first laser component may emit a first laser beam (e.g., the first laser beam 422 described above). The second laser component may emit a second laser beam (e.g., the second laser beam 432 described above).

A target point may be determined based on an intersection between the first laser beam emitted by the first laser component and the second laser component emitted by the second laser component. The region of interest (ROI) of the target subject may be placed at the target point. An anatomical image of the ROI with respect to the first perspective may then be determined.

In some embodiments, the C-arm may be rotated to a second perspective different from the first perspective. The region of interest (ROI) of the target subject may also be placed at the target point. An anatomical image of the ROI with respect to the second perspective may then be determined.

The anatomical images of the ROI with respect to the first perspective and the second perspective may be determined for one time, and the ROI may be near to or at the centers of the anatomical images, thus the operator may not need to adjust the C-arm, a times for scanning may be reduced, the target subject (e.g., a patient) may be avoided from unnecessary radiation, and the working efficiency of the operation may be improved.

Figure 8:
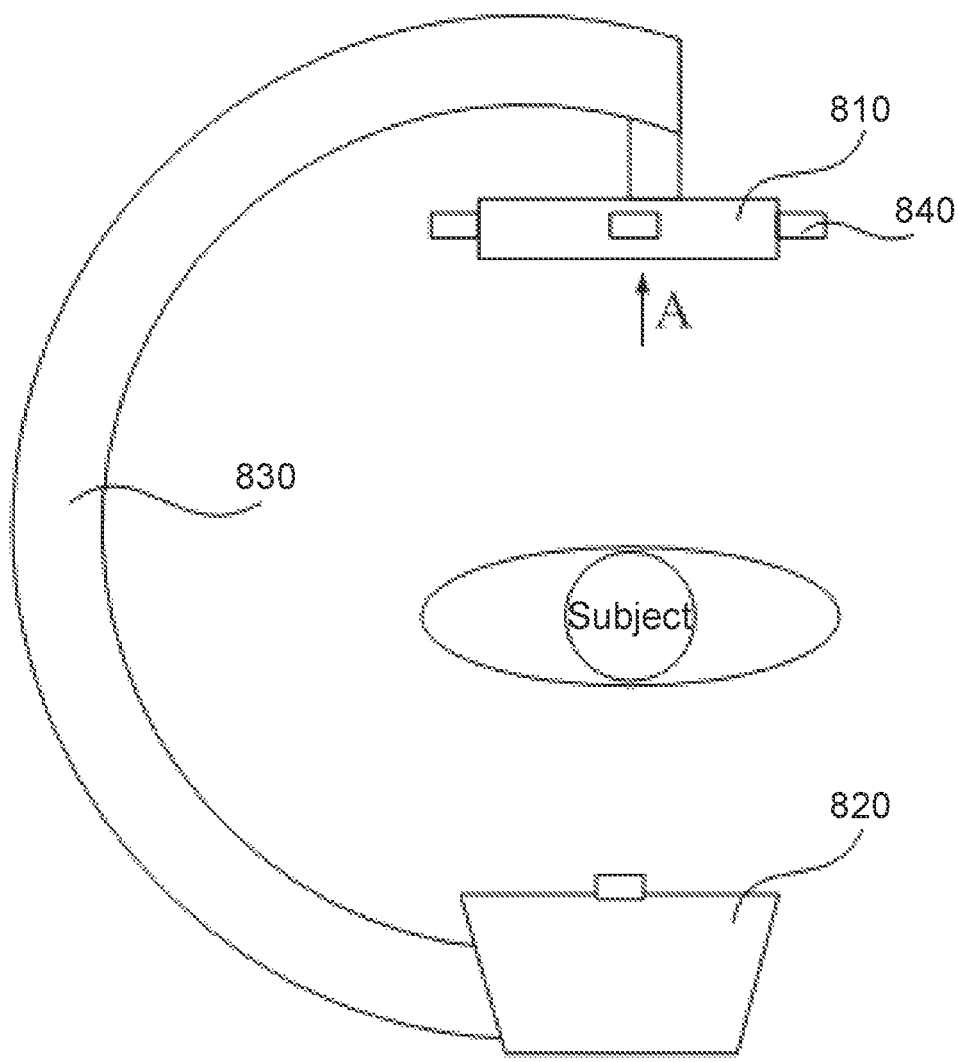
FIGS. 8-9 are schematic diagrams illustrating an exemplary X-ray system according to some embodiments of the present disclosure.
Figure 9:
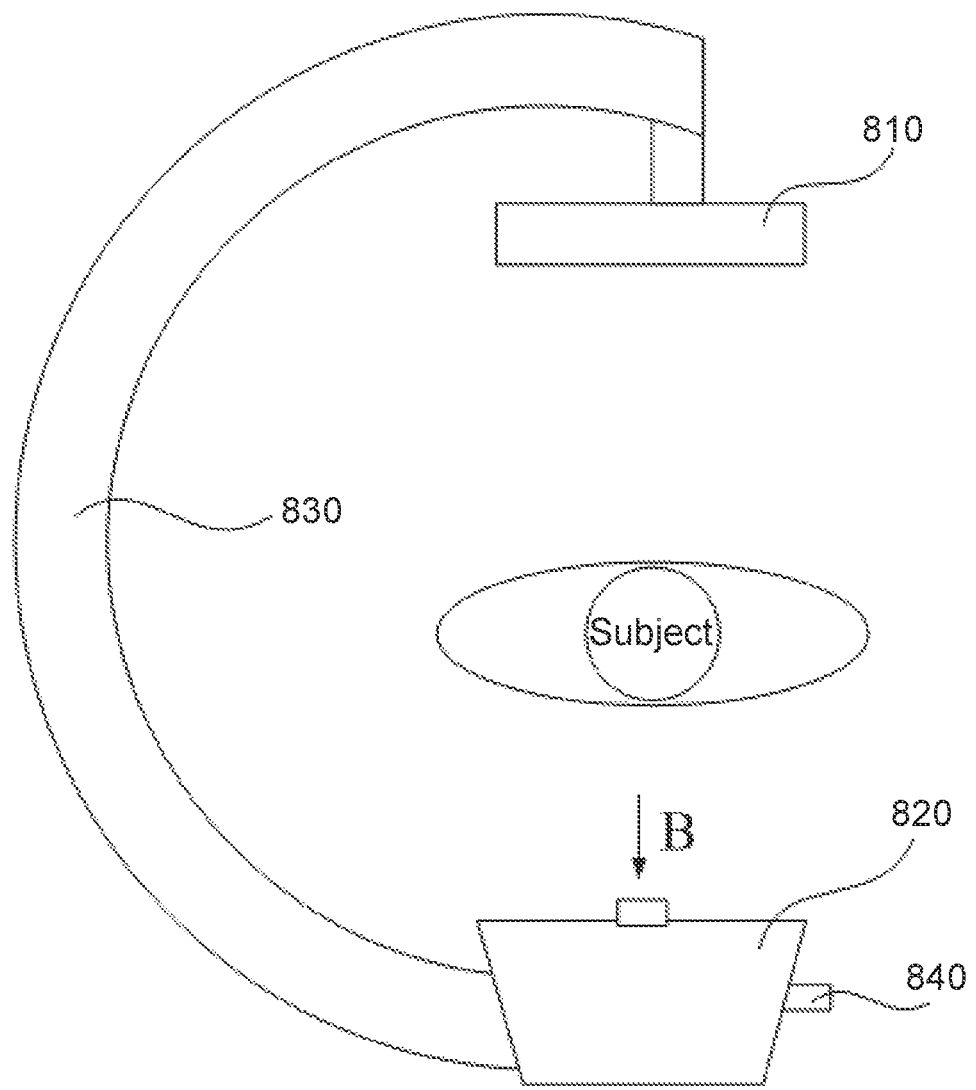

In the prior art, an X-ray system may be configured to scan a target subject and then determine an anatomical image of the target subject. The anatomical image may show a health condition of the target subject, and the anatomical image may be used to help a surgical operation. The X-ray system generally cannot navigate a surgical operation, and thus an additional navigation device may be needed to assist the operator to navigate the surgical operation (e.g., a surgical knife, a location wherein the surgery is performed). In this case, the operator may determine the location of the surgical knife and/or the location where the surgery is performed by repeatedly scanning, which may cause a relatively large amount of radiation to the operator and the target subject and be harmful to them. FIGS. 8-9 are schematic diagrams illustrating an exemplary X-ray system according to some embodiments of the present disclosure. The X-ray system 800 can navigate a surgical operation. The X-ray system 800 may include a detection component 810, an X-ray source 820, a C-arm 830, and a third positioning component 840. The X-ray source 820 may be configured to emit X-rays towards a target subject. The detection component 810 may be configured to receive at least a portion of the X-rays that transmit through the target subject. The C-arm 830 may be configured to support the detection component 810 and the X-ray source 820.

The third positioning component 840 may be configured to obtain location information of a target device associated with the target subject in real-time. The target device may include an operation equipment, e.g., a surgical knife. The third positioning component 840 may include at least two positioning detectors 841.

The third positioning component 840 may be integrated at the X-ray system 800. It should be noted that the third positioning component 840 may be integrated at a position of the X-ray system, from which the surgical operation of the target subject can be monitored. The third positioning component 840 may send the location information of the target device to an image processing station (e.g., the processing device 120). The image processing station may virtually display the location information of the target device on the anatomical image, thereby navigating the surgical operation and guiding the operator to perform the surgical operation.

Figure 10:
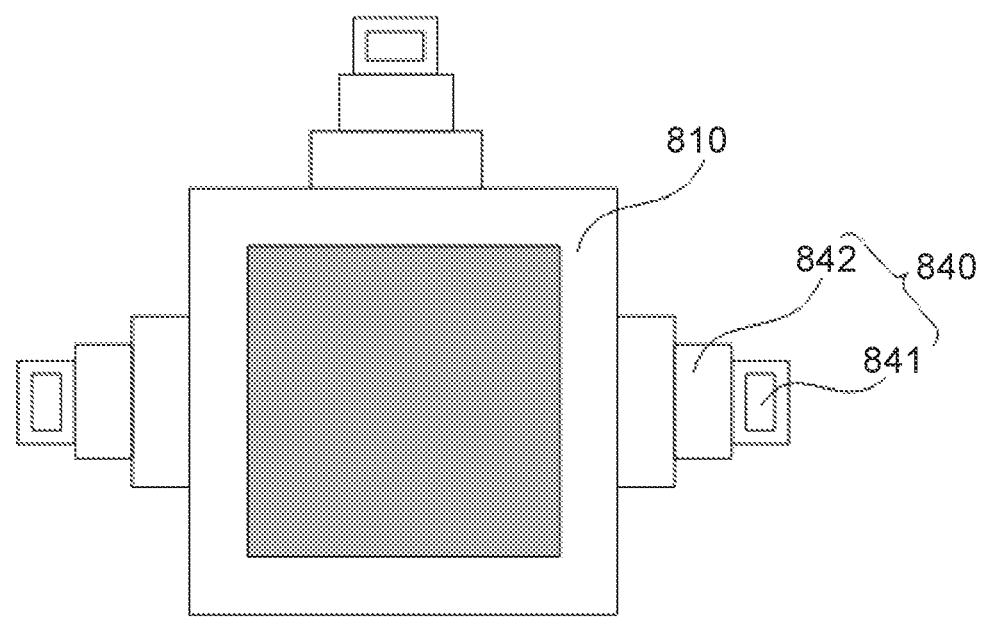
FIGS. 10-11 are schematic diagrams illustrating an exemplary third positioning component according to some embodiments of the present disclosure.
Figure 11:
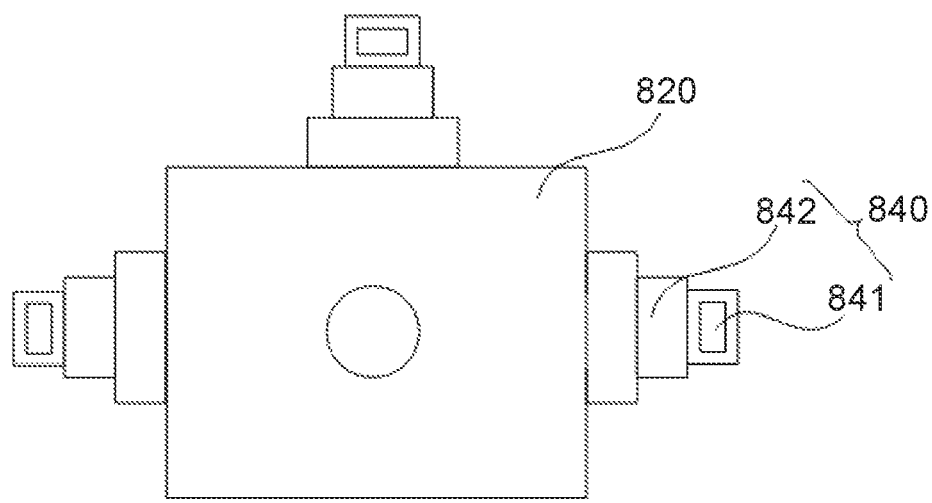

The third positioning component 840 may include at least two positioning detectors (e.g., positioning detector 841 as illustrated in FIGS. 10-11). The positioning detectors may include various kinds of positioning detectors. For example, the positioning detectors may include optic positioning detectors, e.g., infrared detectors. Take the operation equipment as the target device, when the positioning detectors is an infrared detector, the operation equipment may have an infrared source matched with the infrared detector, additionally or alternatively, the operation equipment may have a reflector that can passively reflect infrared rays. The infrared rays emitted or reflected by the operation equipment may be collected by the infrared detector, and thereby obtaining location information of the infrared source or the reflector of the operation equipment in real time. In some embodiments, a length of the operation equipment, a relative position of an end of the operation equipment and the infrared source or the reflector may be predetermined, thereby locating the operation equipment and navigating the surgery. In some embodiments, a locator may be mounted on an end of the operation equipment. The locator may include at least three infrared emitting balls or at least three infrared reflecting balls. The positioning detectors (e.g., cameras) may monitor locations of the at least three infrared emitting balls or the at least three infrared reflecting balls, thereby determining the relative position of the end of the operation equipment.

In some embodiments, the positioning detector may also include laser positioning detectors, high-precision cameras, etc. In some embodiments, the positioning detectors may include non-optical positioning detectors, e.g., magnetic field sensors. The magnetic field sensor may be mounted on the target device. A magnetic field source may generate a magnetic field, and the magnetic field sensor may receive a signal emitted by the magnetic field sensor, thereby obtaining a location and a spatial location and a posture of the magnetic field sensor.

In some embodiments, the third positioning component 840 may be mounted on at least one position of the X-ray system 800. In some embodiments, as shown in FIG. 8, the third positioning component 840 may be mounted on the detection component 810. For example, the third component 400 may be mounted on an end of the detection component 810.

In some embodiments, as shown in FIG. 9, the third positioning component 840 may be mounted on the X-ray source 820. For example, the third component 400 may be mounted on an end of the X-ray source 820.

In some embodiments, the third positioning component 840 may be mounted on the C-arm 830 of the X-ray system 800. The C-arm 830 may rotate along different rotation axes, thereby scanning the target subject from different perspectives. In some embodiment, the third positioning component 840 may be mounted on a position that is relatively near to an end of the C-arm 830, and the position may be at an upper side of the platform such that the third positioning component 840 can navigate the surgical operation.

A space for mounting the positioning detectors may be limited and, distances between different positioning detectors may be not long, causing to inaccurately locate the operation equipment. In some embodiments, the at least two positioning detectors may be able to move to adjust at least two distances between the at least two positioning detectors, thereby ensuring to navigate the surgical operation accurately.

The at least two distances between the at least two positioning detectors may be adjusted by various structures. FIGS. 10-11 are schematic diagrams illustrating an exemplary third positioning component according to some embodiments of the present disclosure. As shown in FIGS. 10-11, the third positioning component 840 may include at least one reciprocating rod 842. An end of each of the at least one reciprocating rod 842 may be mounted on, e.g., the C-arm 830. One positioning detector of the positioning detectors 841 may be mounted on an end that is relatively far from, e.g., the C-arm 830, of one reciprocating rod of the at least one reciprocating rod 842.

In some embodiments, a number of the at least one reciprocating rod 842 may include 1, 2, or more. For example, if the number of the positioning detectors 841 is 2, and a distance between the two positioning detectors 841 needs to be adjusted, one of the two positioning detectors 841 may be mounted on a position of the X-ray system relatively far from the position of the X-ray system 800, and another of the two positioning detectors 841 may be mounted on a position of the X-ray system, thereby adjusting the distance between the two positioning detectors 841. Additionally or alternatively, a number of the at least one reciprocating rod 842 may be 2, and the two positioning detectors 841 may be mounted on an end that is far from the position of the reciprocating rod 842, thereby adjusting the distance between the two positioning detectors 841 by the two reciprocating rods 842.

In some embodiments, the number of the at least one reciprocating rod 842 may correspond to the number of the positioning detectors 841, thereby making the adjustment of at least one distance between the positioning detectors 841 more flexible.

In some embodiments, an end of the reciprocating rod(s) 842 may be directly fixed on a position of the X-ray system 100. For example, the end of the reciprocating rod(s) 842 may be directly fixed on the detection component 810, the X-ray source 820, or the C-arm 830.

In some embodiments, the number of the positioning detectors 841 may be 3, and the number of the corresponding reciprocating rod(s) 842 may also be 3. The three reciprocating rods 842 may be fixed as a whole by an annular holder. The three reciprocating rods 842 may be mounted along the edge of the annular holder, and each of the three reciprocating rods 842 may extend along a plane of the annular holder. An end of the each of the reciprocating rods 842 may be connected to the annular holder. The three positioning detectors 841 may be mounted on the other end of the each of the three reciprocating rods 842. The annular holder may be fitted on the outer periphery of the detection component 810, the outer periphery of the X-ray source 820 or the outer periphery of the C-arm 830.

In some embodiments, the reciprocating rod(s) 842 may be fixed as a whole by a base. When the number of the positioning detectors 841 is 2, the number of the corresponding reciprocating rod(s) 842 may be 2. The two reciprocating rods 842 may be arranged as a shape of slot, a shape of T, a shape of crisscross. An end of each of the two reciprocating rods 842 may be connected to the base. The two positioning detectors 841 may be mounted on the other end of the each of the reciprocating rods 842. The base may be mounted on an outer surface of the shell of the detection component 810, or an inner surface of the shell of the detection component 810. The base may also be mounted on an outer surface of the shell of the detection component 810, or an inner surface of the shell of the X-ray source 820. The base may also be mounted on the C-arm 830.

When the distance between the positioning detectors 841 needs to be adjusted, a reciprocating length of the reciprocating rod(s) 842 may be adjusted, thereby adjusting the distances between two of the positioning detectors 841.

In some embodiments, the reciprocating rod(s) 842 may include a least one electric reciprocating rod, thereby automatically adjusting the distances between the positioning detectors 841. In some embodiments, the at least one electric reciprocating rod may be equipped with at least one encoder, thereby monitoring the adjustment of the distances in real time.

In some embodiments, the positioning detectors 841 may include at least one slide rail. At least two of the positioning detectors 841 may slide through the at least one slide rail.

In some embodiments, the at least one slide rail may be mounted on the detection component 810, the X-ray source 820, or the C-arm 830. Each of the at least one slide rail may have a shape of slot, a shape of T, a shape of crisscross, etc. The at least two of the positioning detectors 841 may slide through the at least one slide rail, thereby adjusting the distances between the positioning detectors 841 based on practical demand. Therefore, the accuracy of the navigation may be improved. In some embodiments the each of the at least one slide rail may include a chute structure, a slide structure.

In some embodiments, the slide rail may include a reciprocating slide rail. Therefore, a range for adjusting the distances between the positioning detectors 841 may be increased and an area of the slide rail may be decreased, e.g., a reciprocating slide-way structure.

The third positioning component 840 may be integrated in the X-ray system directly in the present disclosure, thereby avoiding to place an additional trolley for navigation in an operation room and saving the space of the operation room. When the X-ray system 800 is used for navigation, an anatomical image of the target subject may be first obtained, and the location information of the target subject may be overlapped and displayed on the anatomical image for navigation.

An additional navigation device may need to be registered to an X-ray system in the prior art. Three points on at least one flat detector of the X-ray system may be determined by a positioning pin, and the additional navigation device may collect a spatial location of the flat detector, thereby registering the additional navigation device to the X-ray system. In the present disclosure, the third positioning component 840 may be integrated in the X-ray system 800, and thus the location information of the X-ray system 800 determined by the third positioning component 840 and the anatomical image may have a relatively high compatibility and matching degree. Besides, the image transmission response is relatively fast, thereby improving the accuracy of the navigation effectively.

Figure 12:
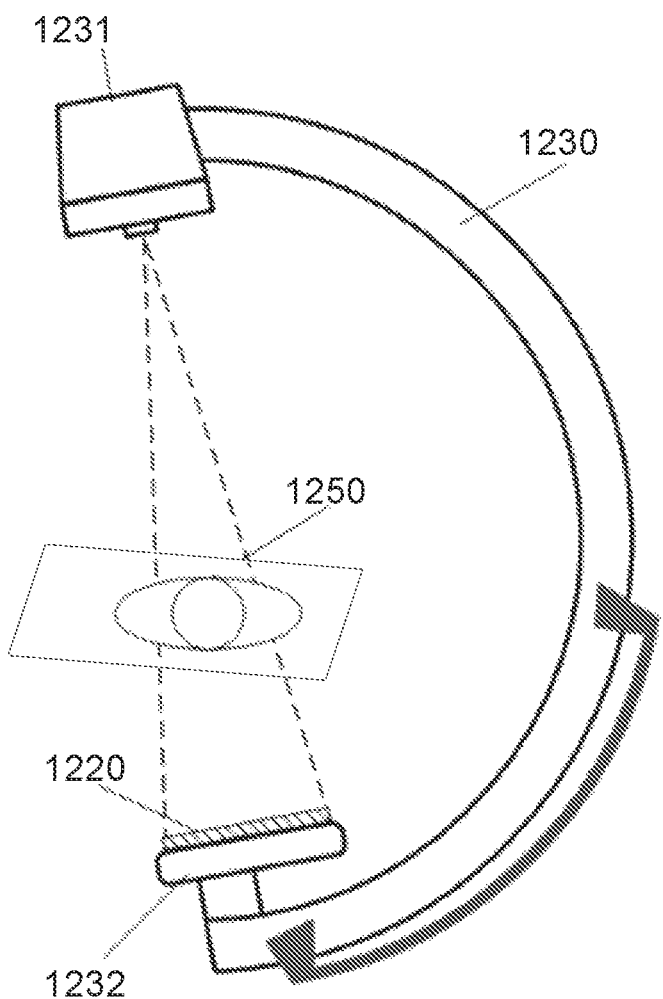
FIG. 12 is a schematic diagram illustrating an exemplary X-ray system according to some embodiments.
Figure 13:
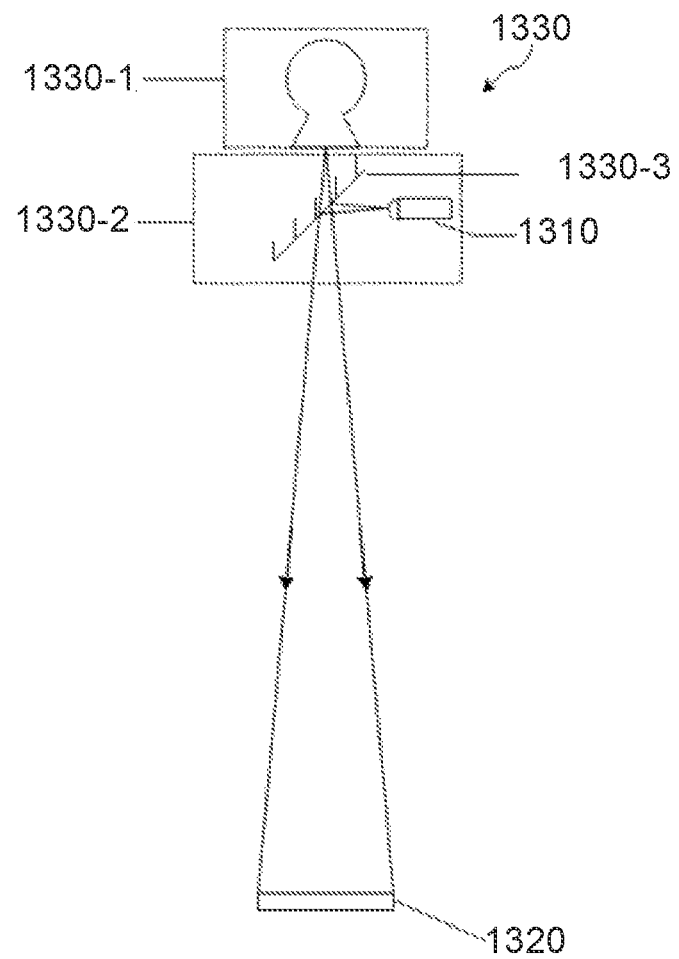
FIG. 13 is a schematic diagram illustrating an exemplary travel path of an X-ray beam emitted by an X-ray source and an exemplary travel path of a first laser beam emitted by a first laser component according to some embodiments of the present disclosure.

FIG. 12 is a schematic diagram illustrating an exemplary X-ray system, and FIG. 13 is a schematic diagram illustrating an exemplary travel path of an X-ray beam emitted by an X-ray source and an exemplary travel path of a first laser beam emitted by a first laser component according to some embodiments of the present disclosure. The X-ray system 1200 may include an X-ray source 1231, a C-arm 1230, a detection component 1232, and a platform 1250. The X-ray source 1231 may be configured to emit X-rays towards a target subject. The detection component 1232 may be configured to receive at least a portion of the X-rays that transmit through the target subject. The platform 1250 may be configured to support the detection component 1232 and the X-ray source. The C-arm 1230 may be configured to support the detection component 1232 and the X-ray source. A portion of the component of the X-ray system 1200 (e.g., the detection component 1232, the platform 1250) may be similar to the components of the X-ray system 400 or 800.

As shown in FIGS. 12-13, the X-ray system 1200 may also include a second positioning component 1220 and a laser emitting component 1310. The laser emitting component 1310 may be mounted on the X-ray source 1231 and configured to emit a laser beam (also referred to as "positioning beam"). The projection of the laser beam on the target subject may have a first predetermined pattern. In some embodiments, a grating with grids may be configured inside the laser emitting component 1310, thereby generating the laser beam of which the projection include grids when the laser beam penetrates the grating. The second positioning component 1220 may be situated between the detection component 1232 and the platform 1250. In some embodiments, the C-arm 1230 may be configured with at least one holder, and the second positioning component 1220 may be fixed by the holder(s). The surface of the second positioning component 1220 may show a pattern.

The X-ray system 1200 may determine at least one anatomical image associated with the target subject by emitting the X-rays towards the target subject. The anatomical image may show a physical condition of the at least a portion of the target subject. If there is something wrong with the at least a portion of the target subject, a lesion point may be determined based on the anatomical image. An overlaid image may be determined by overlapping the pattern and the anatomical image. Before placing the target subject on the platform 1250, the first predetermined pattern may be determined to coincide with or be adjusted to coincide with the pattern of the second positioning component, and a first travel path of the laser beam may be determined to coincide with or be adjusted to coincide with a second travel path of the X-ray beam. A target point may then be determined after the laser emitting component 1310 emits the laser beam towards the target subject based on the anatomical image and the pattern. The target point may be a point corresponding to the lesion point, and a surgical operation may be performed at the target subject. As a result, the X-ray system 1200 described above may facilitate an operator (e.g., a doctor) to locate a target point (e.g., a lesion point) of the target subject.

In some embodiments, as shown in FIG. 13, the X-ray source 1231 may include an X-ray component 1330-1 and a laser controlling component 1330-2. The X-ray component 1330-1 may be configured to emit the X-rays towards the target subject. The laser component 1330-2 may be underneath of the X-ray component 1330-1. The laser component 1330-2 may include a reflector 1330-3 and the laser emitting component 1310. The reflector 1330-3 may be tilted, and the laser emitting component 1310 may be situated on one side of the reflector 1330-3. A travel path of the X-rays emitted by the X-ray component 1330-1 may be the same as a travel path of the X-rays after reflected by the reflector 1330-3. A travel path of the laser emitted by the laser emitting component 1310 may be different from a travel path of the laser after reflected by the reflector 1330-3, and the travel path of the laser after reflected by the reflector 1330-3 may coincide with the travel path of the X-rays emitted by the X-ray component 1330-1. The structure of the X-ray source 1231 described above may ensure that the travel path of the laser after reflected by the reflector 1330-3 may coincide with the travel path of the X-rays emitted by the X-ray component 1330-1 and avoid the laser emitting component 1310 being situated underneath the X-ray component 1330-1, which may cause to shelter a portion of the X-rays. In some embodiments, the laser emitting component 1310 may include a laser lamp. A pattern of laser emitted by the laser lamp may be grids, and the configuration may facilitate the structure of the second positioning component 1220 for determining the target point of the target subject.

In some embodiments, the second positioning component 1220 may be situated on a surface of the detection component 1232 facing the platform 1250, thereby making a distance between the second positioning component 1220 and the detection component 1232 closer. A size of the second positioning component 1220 may be approximately equal to a size of the pattern projected on the detection component 1232, thereby reducing the influence of the amplification on the second positioning component 1220 and improving the accuracy for locating the target point.

In some embodiments, the second positioning component 1220 may be made of (soft) metal, e.g., aluminum, copper. The second positioning component 1220 made of soft metal may have a relatively good flexibility convenient to wind when there is no need to use the second positioning component 1220. The X-ray system 1200 may also include a human-computer interaction module. The human-computer interaction module may be configured to set the second positioning component 1220 in a preoperational mode before a surgery for determining a target point and exit the preoperational mode after the target point is determined. The human-computer interaction module may include an operation panel and an operation button.

The second positioning component 1220 may not be needed to be fixed on the surface of the target subject, thereby simplifying the process for locating the target point of the target subject and improving the efficiency of the operation. The second positioning component 1220 may be situated between the detection component 1232 and the platform 1250, and a ratio for amplifying the grids of the second positioning component 1220 may be relatively small, thus the grids of the second positioning component 1220 may be made relatively more fine than the grids of the prior art. As a result, the target point of the target subject may be located by one time and the result may be more accurately. Besides, a times of emitting the X-ray beam towards the target subject may be reduced.

Figure 14:
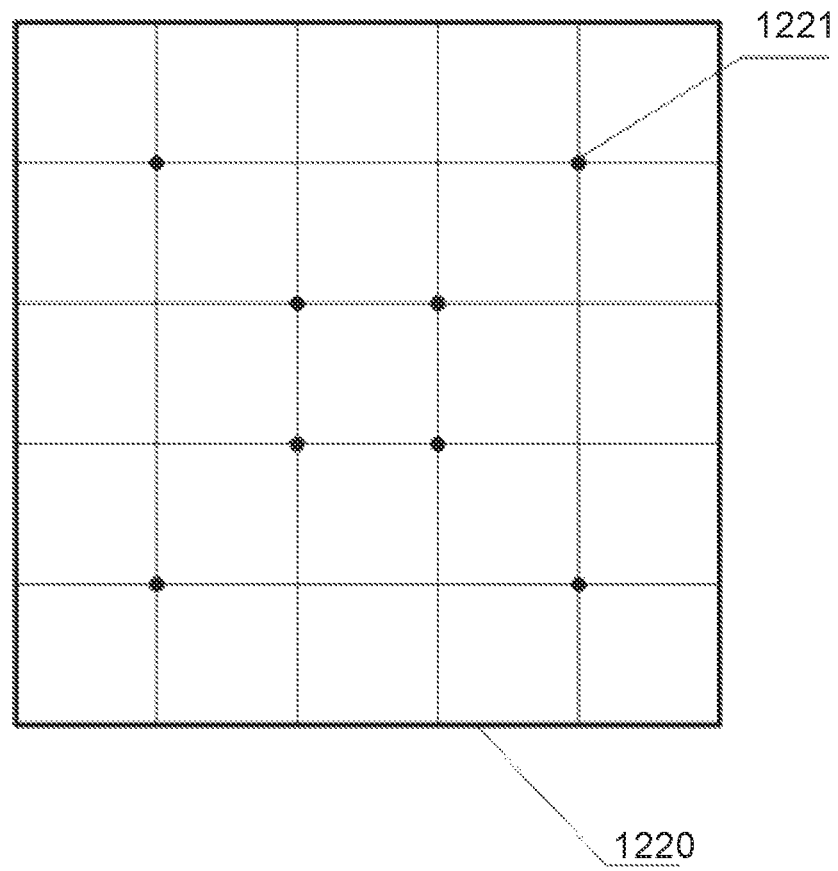
FIG. 14 is a schematic diagram illustrating an exemplary pattern of a second positioning component according to some embodiments.
Figure 15:
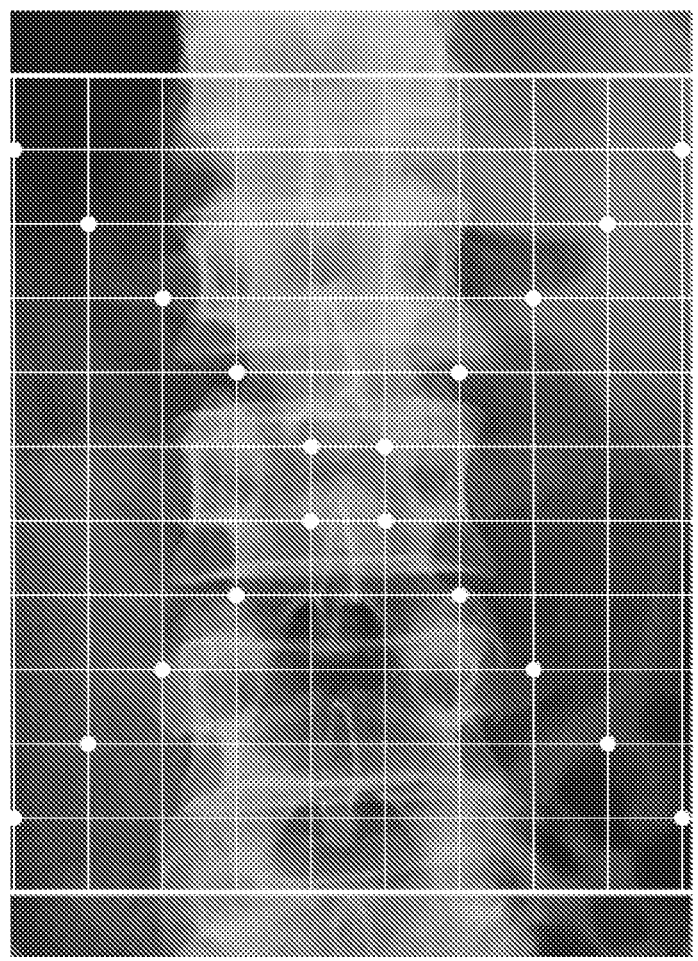
FIG. 15 is a schematic diagram illustrating an exemplary anatomical image associated with the exemplary pattern of the second positioning component according to some embodiments of the present disclosure.

FIG. 14 is a schematic diagram illustrating an exemplary pattern of a second positioning component, and FIG. 15 is a schematic diagram illustrating an exemplary anatomical image associated with the exemplary pattern of the second positioning component according to some embodiments of the present disclosure.

The pattern may include at least one laser marker (not shown in FIGS. 12-15). The at least one laser marker may be marked on the grating with grids. The at least one laser marker may be arranged at intersections of the grids according to a predetermined form. For example, the at least one laser marker may be arranged in a form of crisscross at the intersections of the grids. The second positioning component 1220 may also include at least one positioning marker 1221. Each of the positioning marker(s) 1221 may correspond to one of the at least one laser marker. The configuration of the positioning marker(s) 1221 may facilitate the operator to locate the target point of the target subject based on the anatomical image. The at least one laser marker projected on the target subject may facilitate the operator to locate the target point (e.g., a puncturing point) of the target subject for the operation (e.g., a puncturing surgery). As shown in FIGS. 14-15, the positioning marker(s) 1221 may be arranged in a form of crisscross at the intersections of the grids. It should be noted that the above description of the arrangement of the positioning marker(s) 1221 is provided for the purpose of illustration, and is not intended to limit the scope of the present disclosure. The arrangement of the positioning marker(s) 1221 may be in any other suitable form. Additionally, a shape of the grids of the second positioning component 1220 and/or the grids of the laser beam may include triangle, square, quadrangle, polygon, circle, curve, concentric circles, etc. When the shape of the grids is square, it may facilitate the operator to observe and locate the target point of the target subject.

FIGS. 16-19 are schematic diagram illustrating exemplary second positioning components according to some embodiments of the present disclosure.

Figure 16:
FIGS. 16-19 are schematic diagram illustrating exemplary second positioning components according to some embodiments of the present disclosure.
Figure 17:
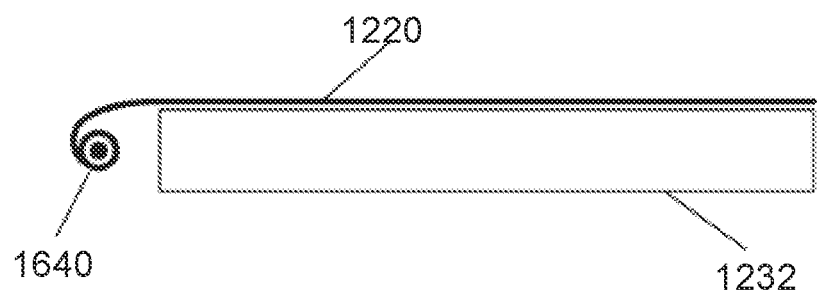
Figure 18:
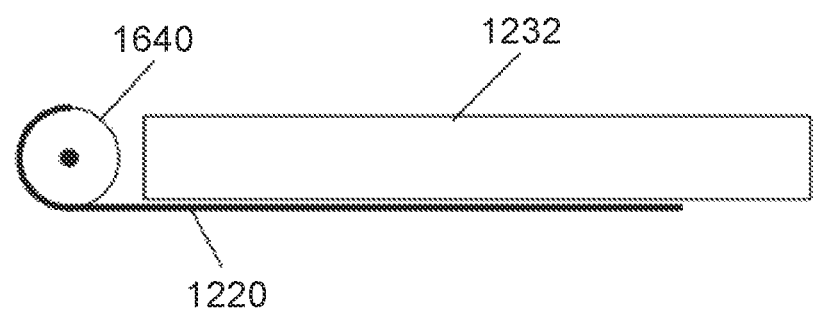
Figure 19:
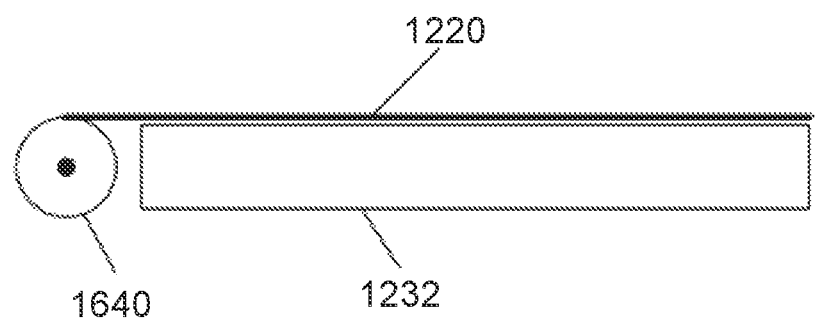

As shown in FIGS. 16-19, the X-ray system 1200 may include a movement device. The movement device may be configured to move the second positioning component 1220 away from the surface of the detection component 1232 facing the platform 1250. For example, the movement device may move the second positioning component 1220 by machine hands, cylinders, etc. In some embodiments, the movement device may include a transmission mechanism 1640. The transmission mechanism 1640 may be configured to place the second positioning component 1220 on the detection component 1232 upon entering the preoperational mode, and wind the second positioning component 1220 on the detection component 1232 upon exiting the preoperational mode. The transmission mechanism 1640 may include at least one transmission wheel. The at least one transmission wheel may be connected to the second positioning component 1220. In some embodiments, as shown in FIGS. 16-17, an end of the second positioning component 1220 may be fixed on the transmission wheel. Upon detecting entering the preoperational mode, the transmission mechanism 1640 may pull out the second positioning component 1220. Upon detecting exiting the preoperational mode, the transmission mechanism 1640 may wind the second positioning component 1220 on the transmission wheel. In some embodiments, as shown in FIGS. 18-19, when the second positioning component 1220 is in use, the transmission mechanism 1640 may place the second positioning component 1220 on the detection component 1232. When there is no need to use the second positioning component 1220, the transmission mechanism 1640 may hide the second positioning component 1220 on a surface of the detection component 1232 back to the platform 1250. It should be noted that the above description of the transmission mechanism 1640 is provided for the purpose of illustration, and is not intended to limit the scope of the present disclosure. The transmission mechanism 1640 may include any suitable structure that makes the second positioning component 1220 placed or wounded. The configuration of the transmission mechanism 1640 may facilitate the user of the X-ray system and shorten a time for an operator to perform a surgery. Besides, the second positioning component 1220 may have little influence on normal process for generating an anatomical image associated with the target subject, thereby improving the applicability of the X-ray system.

Figure 20:
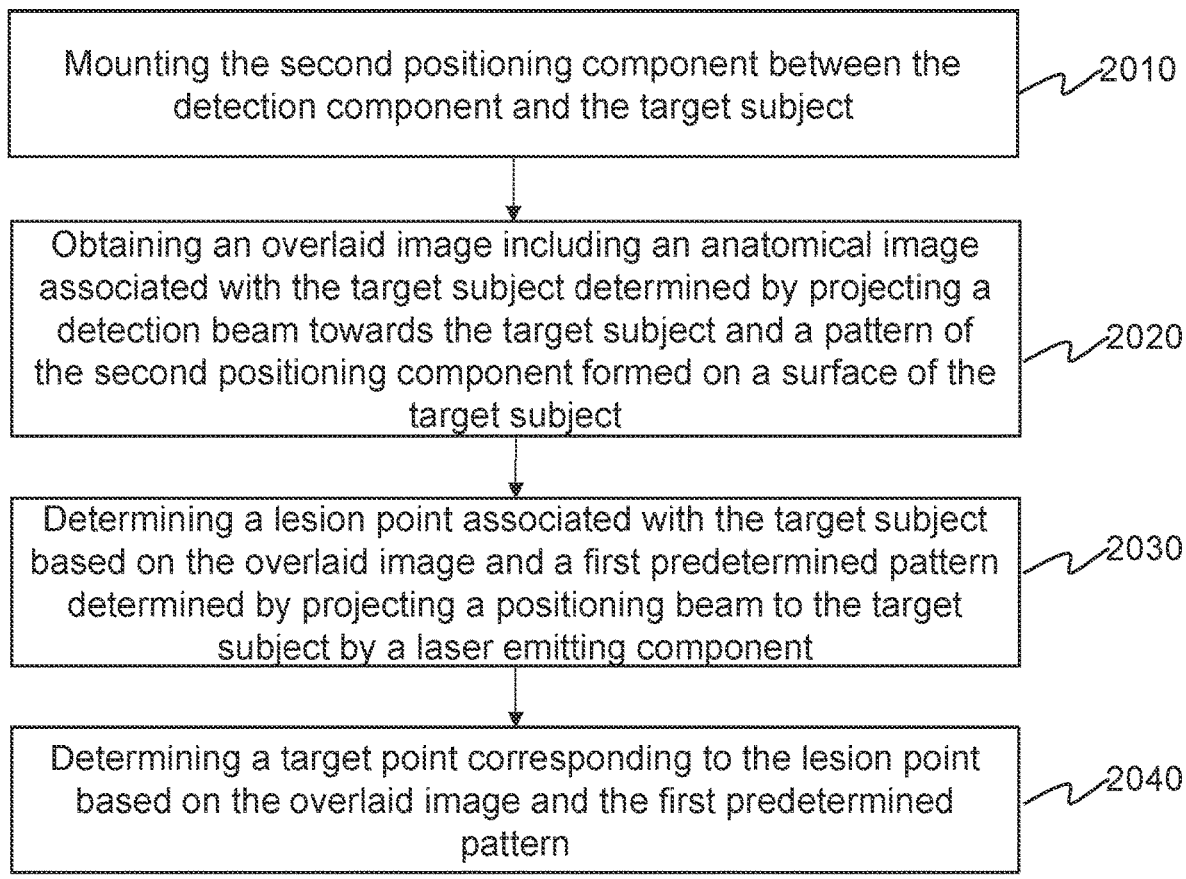
FIG. 20 is a flowchart illustrating an exemplary process for determining a target point according to some embodiments of the present disclosure.

FIG. 20 is a flowchart illustrating an exemplary process for determining a target point according to some embodiments of the present disclosure.

In 2010, the second positioning component 1220 may be mounted between the detection component 1232 and the target subject. In some embodiments, the transmission mechanism 1640 may move the second positioning component 1220 to the surface of the detection component 1232 facing to the target subject upon detecting that a preoperational mode is set.

In 2020, an overlaid image may be obtained. The overlaid image may include an anatomical image associated with the target subject and a pattern of the second positioning component 1220 formed on a surface of the target subject. In some embodiments, the anatomical image may be determined by projecting a detection beam towards the target subject.

In 2030, a lesion point associated with the target subject may be determined based on the anatomical image or the overlaid image. In 2040, a target point corresponding to the lesion point may be determined based on the overlaid image and a first predetermined pattern determined by projecting a positioning beam to the target subject. The positioning beam may be emitted by the laser emitting component. After the target point is determined, the preoperational mode may exist, and an operator may perform a surgical operation at or around the target point.

The target point may be determined based on a relationship between the first predetermined pattern and the pattern of second positioning component 1220, thereby improving the accuracy and reduce an operation time of determining the target point for the operator and reducing a times of radiation towards the target subject.

Figure 21:
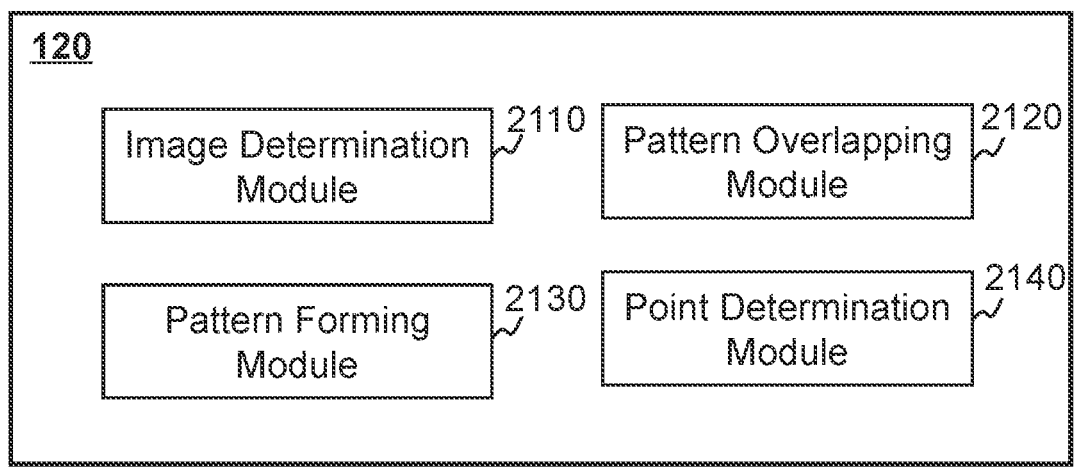
FIG. 21 is a block diagram illustrating an exemplary processing device 120 according to some embodiments of the present disclosure

FIG. 21 is a block diagram illustrating an exemplary processing device 120 according to some embodiments of the present disclosure. The processing device 120 may include an image determination module 2110, a pattern overlapping module 2120, a pattern forming module 2130, and a point determination module 2140.

The image determination module 2110 may be configured to determine an anatomical image associated with a target subject. The anatomical image may show a physical condition of at least a portion of the target subject. In some embodiments, the image determination module 2110 may determine the anatomical image by projecting a detection beam towards the target subject. The image determination module 2110 may project the detection beam upon obtaining an instruction for projecting the detection beam.

The pattern overlapping module 2120 may be configured to overlap a first pattern on the anatomical image. The first pattern may include a plurality of first repeated shapes. The anatomical image may be divided into a plurality of portions by the first repeated shapes. The first pattern can be used to mark at least one point (e.g., a lesion point) of the target subject based on the first repeated shapes. In some embodiments, the pattern overlapping module 2120 may determine at least one location of the at least one point of the target subject relative to any reference element of the first pattern. For example, the reference element may include a point on the first pattern, a line on the first pattern, etc. In some embodiments, the first pattern may include at least one marker. The at least one marker may be used to mark the at least one point (e.g., a lesion point) of the target subject. The at least one marker may include intersecting points of the grids, short lines, circles, etc.

The pattern forming module 2130 may be configured to form a second pattern on the surface of the target subject by projecting a positioning beam to the target subject. The positioning beam may be a laser beam. The laser beam may be an array of induced photons. The second pattern may include a plurality of second repeated shapes, and the second pattern may coincide with the first pattern. In some embodiments, the size of each first repeated shape of the first pattern may be proportional with the size of each second repeated shape of the second pattern, e.g., 1.5:1, 1.2:1, etc.

The point determination module 2140 may be configured to determine a target point based on the anatomical image and the second pattern. The target point may be a point where a surgical operation is performed.

In some embodiments, the point determination module 2140 may determine a lesion point associated with the target subject based on the anatomical image. If there is something wrong with the at least a portion of the target subject, a lesion point may be determined based on the anatomical image. The point determination module 2140 may then determine the target point on the grids of the second pattern based on the lesion point. The target point may be a point on the second pattern or the surface of the target subject corresponding to the lesion point on the anatomical image and the first pattern.

In some embodiments, the point determination module 2140 may first determine a relationship between a plurality of first points on the grids of the first pattern and a plurality of second points corresponding to the plurality of first points on the grids of the second pattern. For example, the relationship may include a direct proportional relationship (e.g., 1.5:1, 1.2:1), an inverse proportional relationship, a logarithmic relationship, etc. The point determination module 2140 may then determine the target point on the grids of the second pattern based on the lesion point and the relationship.

In some embodiments, the point determination module 2140 may obtain diagnostic information associated with the target subject. The diagnostic information may be associated with the anatomical image, or any other examination result associated with the target subject that represents the physical condition of the at least a portion of the target subject. The point determination module 2140 may then determine the lesion point associated with the target subject based on the diagnostic information.

Figure 22:
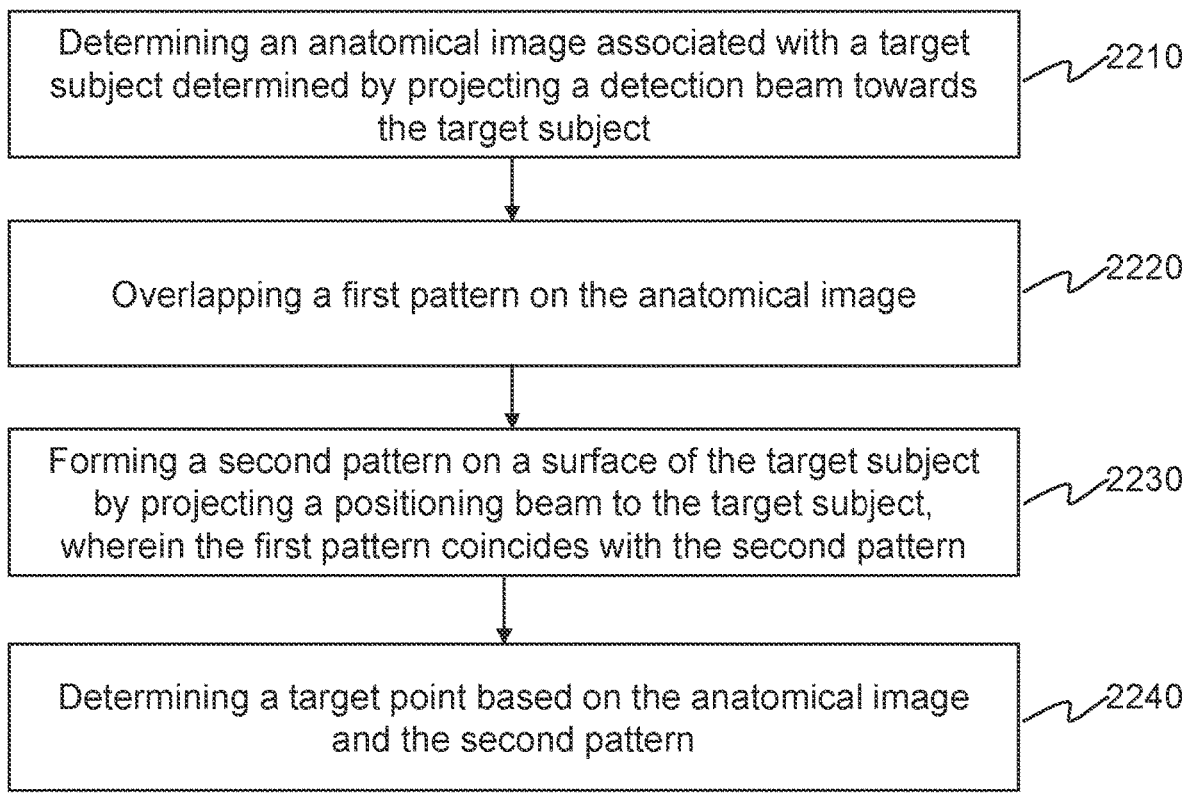
FIG. 22 is a flowchart illustrating an exemplary process for determining a target point of an X-ray system according to some embodiments of the present disclosure.

FIG. 22 is a flowchart illustrating an exemplary process for determining a target point of an X-ray system according to some embodiments of the present disclosure. The X-ray system may include an X-ray source, a C-arm, a detection component, and a platform. The function of the X-ray source, the C-arm, the detection component, and the platform may be similar to the X-ray source, the C-arm, the detection component, and the platform described in the X-ray system 400, the X-ray system 800, or the X-ray system 1200.

The X-ray source may further include an X-ray component, a laser controlling component, and a reflector. The structure and the function of the X-ray component, the laser controlling component and the reflector may be similar to the X-ray component 1330-1, the laser controlling component 1330-2 and the reflector 1330-3 respectively. As shown in FIG. 13, the laser controlling component 1330-2 may be situated at one side of the X-ray component 1330-1 and not be situated within a range that the X-ray component 1330-1 emits the X-rays, thereby avoiding sheltering at least a portion of the X-rays. In some embodiments, the reflector 1330-3 may be situated within the range that the X-ray component 1330-1 emits the X-rays. A travel path of a laser beam emitted by the laser emitting component may be changed upon passing through the reflector, and the changed travel path may coincide with a travel path of an X-ray beam emitted by the X-ray source.

In 2210, the image determination module 2110 may determine an anatomical image associated with a target subject. The anatomical image may show a physical condition of at least a portion of the target subject.

The image determination module 2110 may determine the anatomical image by projecting a detection beam towards the target subject. The detection beam may be the X-ray beam emitted by the X-ray source. The X-ray beam may be a particle flow caused by the transition of electrons between two energy levels with widely different energy levels in an atom. The X-ray beam may be an electromagnetic wave having a wavelength between ultraviolet rays and gamma rays.

The image determination module 2110 may project the detection beam upon obtaining an instruction for projecting the detection beam. In some embodiments, the instruction may be automatically generated upon detecting that the target subject is placed at the platform. In some embodiments, the instruction may be automatically generated upon detecting that the target subject has been placed at the platform and has not been moved for a predetermined time. In some embodiments, the instruction may be generated by an operator (e.g., a doctor) via the network 150.

In 2220, the pattern overlapping module 2120 may overlap a first pattern on the anatomical image. The first pattern may include a plurality of first repeated shapes. The anatomical image may be divided into a plurality of portions by the first repeated shapes. The first pattern can be used to mark at least one point (e.g., a lesion point) of the target subject based on the first repeated shapes. In some embodiments, the pattern overlapping module 2120 may determine at least one location of the at least one point of the target subject relative to any reference element of the first pattern. For example, the reference element may include a point on the first pattern, a line on the first pattern, etc. In some embodiments, the first pattern may include at least one marker. The at least one marker may be used to mark the at least one point (e.g., a lesion point) of the target subject. The at least one marker may include intersecting points of the grids, short lines, circles, etc.

In 2230, the pattern forming module 2130 may form a second pattern on the surface of the target subject by projecting a positioning beam to the target subject. The positioning beam may be a laser beam. The laser beam may be an array of induced photons. The second pattern may include a plurality of second repeated shapes, and the second pattern may coincide with the first pattern. In some embodiments, the size of each first repeated shape of the first pattern may be proportional with the size of each second repeated shape of the second pattern, e.g., 1.5:1, 1.2:1, etc.

In some embodiments, the first pattern or the second pattern may include grids. For example, the grids may include grids including regular polygons, girds including irregular polygons, girds including circles, etc. As another example, the first pattern or the second pattern may include a plurality of closed shapes arranged from outside to inside. The closed shapes may include circles, regular polygons, irregular polygons, etc. It should be noted that the above description of the first pattern and/or the second pattern is provided for the purpose of illustration, and is not intended to limit the scope of the present disclosure. The first pattern and/or the second pattern may include any pattern with suitable shapes.

In some embodiments, the pattern forming module 2130 may project the positioning beam upon obtaining an instruction for projecting the positioning beam. In some embodiments, the instruction may be automatically generated upon detecting that the target subject is placed at the platform. In some embodiments, the instruction may be automatically generated upon detecting that the target subject has been placed at the platform and has not been moved for a predetermined time. In some embodiments, the instruction may be generated by an operator via the network 150.

In some embodiments, the pattern forming module 2130 may form a second pattern on the surface of the target subject by projecting a marking beam to the target subject. The marking beam may be emitted by a laser device (e.g., the laser emitting component, a laser lamp) mounted on the C-arm.

In 2240, the point determination module 2140 may determine a target point based on the anatomical image and the second pattern. The target point may be a point where a surgical operation is performed.

In some embodiments, the positioning beam may be adjusted based on the first pattern and the second pattern projected by the positioning beam. When no target subject is placed on the platform, the second pattern projected by the positioning beam may need to coincide with the first pattern such that the target point may be determined based on the lesion point. In some embodiments, a metallic grating with grids may be placed on the surface of the detection component. A reference image may be obtained by emitting the X-rays towards the grating. The reference image may include the first pattern. After emitting the positioning beam towards the grating, a relationship between the first pattern and the second pattern may be determined. The positioning beam may be adjusted if the second pattern does not coincide with the first pattern on the reference image.

It should be noted that the above description is provided for the purpose of illustration, and is not intended to limit the scope of the present disclosure. For persons having ordinary skills in the art, multiple variations and modifications may be made under the teaching of the present disclosure. However, those variations and modifications do not depart from the scope of the present disclosure. For example, the detection beam and the positioning beam may be emitted simultaneously. As another example, the positioning beam may be emitted before the detection beam.

Figure 23:
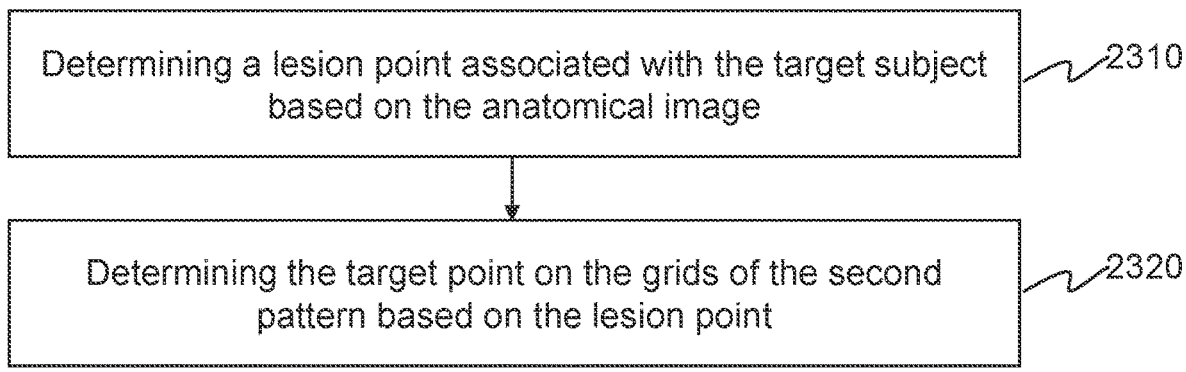
FIG. 23 is a flowchart illustrating an exemplary process for determining a target point associated with a target subject according to some embodiments of the present disclosure.

FIG. 23 is a flowchart illustrating an exemplary process for determining a target point associated with a target subject according to some embodiments of the present disclosure.

In 2310, the point determination module 2140 may determine a lesion point associated with the target subject based on the anatomical image. As described in 2210, the anatomical image may show the physical condition of the at least a portion of the target subject. If there is something wrong with the at least a portion of the target subject, a lesion point may be determined based on the anatomical image. Since the first pattern is overlapped with the anatomical image, the location of the lesion point may be marked on the first pattern.

In 2320, the point determination module 2140 may determine the target point on the girds of the second pattern based on the lesion point. The target point may be a point on the second pattern or the surface of the target subject corresponding to the lesion point on the anatomical image and the first pattern, and the point determination module 2140 may determine the target point based on the lesion point.

In some embodiments, the point determination module 2140 may first determine a relationship between a plurality of first points on the grids of the first pattern and a plurality of second points corresponding to the plurality of first points on the grids of the second pattern. For example, the relationship may include a direct proportional relationship (e.g., 1.5:1, 1.2:1), an inverse proportional relationship, a logarithmic relationship, etc. The point determination module 2140 may then determine the target point on the grids of the second pattern based on the lesion point and the relationship. Therefore, the target point may be determined automatically by the X-ray system, which may avoid the risk of estimating the target point by the operator, improving the efficiency of determining the target point and reducing the cost.

Figure 24:
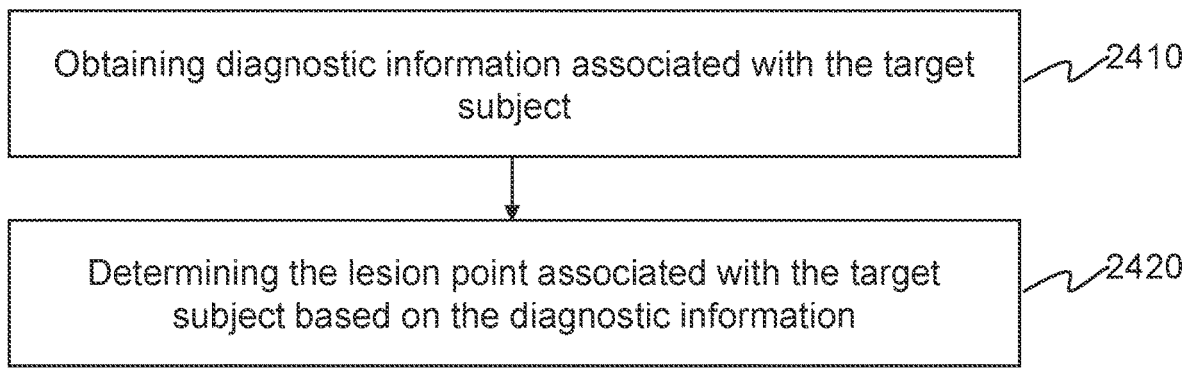
FIG. 24 is a flowchart illustrating an exemplary process for determining a lesion point associated with a target subject according to some embodiments of the present disclosure.

FIG. 24 is a flowchart illustrating an exemplary process for determining a lesion point associated with a target subject according to some embodiments of the present disclosure.

In 2410, the point determination module 2140 may obtain diagnostic information associated with the target subject. The diagnostic information may be associated with the anatomical image determined in 2210, or any other examination result associated with the target subject that represents the physical condition of the at least a portion of the target subject. In 2420, the point determination module 2140 may determine the lesion point associated with the target subject based on the diagnostic information.

In some embodiments, the point determination module 2140 may show the diagnostic information associated with the target subject on the anatomical image. For example, the point determination module 2140 may show the diagnostic information at one side of the lesion point. It may facilitate the operator to explicit the diagnostic information or share the diagnostic information with other remote operators. As a result, it may save time for the surgical operation and improve safety probabilities for emergent patients.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A positioning method of an X-ray system, the X-ray system including an X-ray source and a laser emitting component, and the positioning method comprising:
   determining an anatomical image associated with a target subject by projecting a detection beam towards the target subject using the X-ray source;
   generating an overlaid image by overlapping a first pattern on the anatomical image;
   forming a second pattern on a surface of the target subject by projecting a positioning beam to the target subject using the laser emitting component, wherein the first pattern coincides with the second pattern; and
   determining a target point based on the overlaid image and the second pattern, comprising:
      determining a lesion point associated with the target subject based on the overlaid image; and
      determining the target point on the second pattern based on the lesion point.

2. The positioning method of claim 1, wherein
   the first pattern and the second pattern include grids, or
   the first pattern and the second pattern include closed shapes.

3. The positioning method of claim 1, wherein the determining a lesion point associated with the target subject based on the overlaid image includes:
   determining a location of the lesion point relative to at least one reference element of the first pattern based on the overlaid image.

4. The positioning method of 1, wherein determining the target point on the second pattern based on the lesion point includes:
   determining a relationship between a plurality of first points of the first pattern and a plurality of second points of the second pattern; and
   determining the target point on the second pattern based on the lesion point and the relationship.

5. The positioning method of claim 4, wherein
   the first pattern includes a plurality of first shapes,
   the second pattern includes a plurality of second shapes, and
   the relationship between the first pattern and the second pattern includes a ratio of a size of one of the plurality of first shapes to a size of one of the plurality of second shapes.

6. The positioning method of claim 1, further comprising:
   marking the target point by projecting a marking beam or the positioning beam to the target point.

7. The positioning method of claim 6, wherein the marking beam is emitted by the laser emitting component mounted on an arm of the X-ray system.

8. The positioning method of claim 1, wherein the target point is a point where a surgical operation is performed.

9. The positioning method of claim 1, further comprising:
   adjusting the positioning beam based on the first pattern and the second pattern.

10. The positioning method of claim 9, wherein the adjusting the positioning beam based on the first pattern and the second pattern includes:
    adjusting the positioning beam if the second pattern projected by the positioning beam does not coincide with the first pattern.

11. A positioning system, comprising:
    at least one storage device storing a set of instructions for performing positioning method of an X-ray system, the X-ray system including an X-ray source and a laser emitting component; and
    at least one processor configured to communicate with the at least one storage device, wherein when executing the set of instructions, the at least one processor is configured to direct the system to perform operations including:
    determining an anatomical image associated with a target subject by projecting a detection beam towards the target subject using the X-ray source;
    generating an overlaid image by overlapping a first pattern on the anatomical image;
    forming a second pattern on a surface of the target subject by projecting a positioning beam to the target subject using the laser emitting component, wherein the first pattern coincides with the second pattern; and
    determining a target point based on the overlaid image and the second pattern, comprising:
       determining a lesion point associated with the target subject based on the overlaid image; and
       determining the target point on the second pattern based on the lesion point.

12. The positioning system of claim 11, wherein
    the first pattern and the second pattern include grids, or
    the first pattern and the second pattern include closed shapes.

13. The positioning system of claim 11, wherein the determining a lesion point associated with the target subject based on the overlaid image includes:
    determining a location of the lesion point relative to at least one reference element of the first pattern based on the overlaid image.

14. The positioning system of 11, wherein determining the target point on the second pattern based on the lesion point includes:
    determining a relationship between a plurality of first points of the first pattern and a plurality of second points of the second pattern; and
    determining the target point on the second pattern based on the lesion point and the relationship.

15. The positioning system of claim 14, wherein
    the first pattern includes a plurality of first shapes,
    the second pattern includes a plurality of second shapes, and
    the relationship between the first pattern and the second pattern includes a ratio of a size of one of the plurality of first shapes to a size of one of the plurality of second shapes.

16. The positioning system of claim 11, further comprising:
    marking the target point by projecting a marking beam or the positioning beam to the target point.

17. The positioning system of claim 11, wherein the target point is a point where a surgical operation is performed.

18. A non-transitory computer readable medium, comprising a set of instructions for performing positioning method of an X-ray system, the X-ray system including an X-ray source and a laser emitting component, wherein when executed by at least one processor, the set of instructions direct the at least one processor to effectuate a method, the method comprising:
- determining an anatomical image associated with a target subject by projecting a detection beam towards the target subject using the X-ray source;
- generating an overlaid image by overlapping a first pattern on the anatomical image;
- forming a second pattern on a surface of the target subject by projecting a positioning beam to the target subject using the laser emitting component, wherein the first pattern coincides with the second pattern; and
- determining a target point based on the overlaid image and the second pattern, comprising:
  - determining a lesion point associated with the target subject based on the overlaid image; and
  - determining the target point on the second pattern based on the lesion point.

* * * * *